US011474097B2

(12) United States Patent
An et al.

(10) Patent No.: US 11,474,097 B2
(45) Date of Patent: Oct. 18, 2022

(54) METHOD OF IDENTIFYING A COMPOUND WHICH AFFECTS THE MULTIENZYME METABOLIC ASSEMBLY OF GLUCOSE METABOLISM AND ITS ASSOCIATION WITH CELL CYCLE PROGRESSION IN CANCER CELLS

(71) Applicants: UNIVERSITY OF MARYLAND, BALTIMORE COUNTY, Baltimore, MD (US); NATIONAL INSTITUTES OF HEALTH, Bethesda, MD (US)

(72) Inventors: Songon An, Ellicott City, MD (US); Danielle L. Schmitt, San Diego, CA (US); James Inglese, Bethesda, MD (US); Patricia Dranchak, Gaithersburg, MD (US)

(73) Assignees: UNIVERSITY OF MARYLAND, BALTIMORE COUNTY, Baltimore, MD (US); NATIONAL INSTITUTES OF HEALTH, Bethesda, MD (US)

( * ) Notice: Subject to any disclaimer, the term of this patent is extended or adjusted under 35 U.S.C. 154(b) by 784 days.

(21) Appl. No.: 16/452,767

(22) Filed: Jun. 26, 2019

(65) Prior Publication Data

US 2019/0391135 A1    Dec. 26, 2019

Related U.S. Application Data

(60) Provisional application No. 62/690,027, filed on Jun. 26, 2018.

(51) Int. Cl.
*G01N 33/50*    (2006.01)
*G01N 21/64*    (2006.01)
*C12N 15/85*    (2006.01)

(52) U.S. Cl.
CPC ......... *G01N 33/5035* (2013.01); *C12N 15/85* (2013.01); *C12Y 207/01011* (2013.01); *G01N 21/6428* (2013.01); *G01N 33/5011* (2013.01); *G01N 2021/6439* (2013.01); *G01N 2333/91215* (2013.01)

(58) Field of Classification Search
CPC .......... G01N 33/5035; G01N 21/6428; G01N 33/5011; G01N 2021/6439; G01N 2333/91215; C12Y 207/01011
See application file for complete search history.

(56) References Cited

PUBLICATIONS

Smith, J.A., Poteet-Smith, C.E., Xu, Y., Errington, T.M., Hecht, S.M., and Lannigan, D.A. (2005). Identification of the first specific inhibitor of p90 ribosomal S6 kinase (RSK) reveals an unexpected role for RSK in cancer cell proliferation. Cancer Research, 65, 1027-1034.

Southall, NT, Jadhav, A., Huang, R., Nguyen, T., and Wang, Y. (2009). Enabling the Large-Scale Analysis of Quantitative High-Throughput Screening Data. In Handbook of Drug Screening, (Boca Raton: books.google.co), Seethala, R., Zhang, L., eds., pp. 442-464. Cannot Locate Reference.

(Continued)

*Primary Examiner* — Jeremy C Flinders
(74) *Attorney, Agent, or Firm* — Tristan A. Fuierer; Casimir Jones. S.C.

(57) ABSTRACT

A cell-based quantitative high-throughput screening assay to monitor the formation of PFK1-mEGFP clusters by the action of small molecules to identify small molecules that promote intracellular PFK1 clustering in a cell cycle-dependent manner and may be used to treat cancer.

11 Claims, 11 Drawing Sheets

(56) References Cited

PUBLICATIONS

Tandon, P., Gallo, C.A., Khatri, S., Barger, J.F., Yepiskoposyan, H., and Plas, D.R. (2011). Requirement for ribosomal protein S6 kinase 1 to mediate glycolysis and apoptosis resistance induced by Pten deficiency. Proc. Natl. Acad. Sci. U.S.A., 108, 2361-2365.
Uchiyama, H., Sowa, Y., Wakada, M., Yogosawa, M., Nakanishi, R., Horinaka, M., Shimazaki, C., Taniwaki, M., and Sakai, T. (2010). Cyclin-dependent kinase inhibitor SU9516 enhances sensitivity to methotrexate in human T-cell leukemia Jurkat cells. Cancer Science, 101, 728-734.
Varoni, E.M., Faro, Lo, A.F., Sharifi-Rad, J., and Iriti, M. (2016). Anticancer Molecular Mechanisms of Resveratrol. Front. Nutr., doi: 10.3389/fnut.2016.00008.
Wang, B.-Y., Liu, Q.-Y., Cao, J., Chen, J.-W., and Liu, Z.-S. (2016). Selective CDK7 inhibition with BS-181 suppresses cell proliferation and induces cell cycle arrest and apoptosis in gastric cancer. Drug Des Devel Ther, 10, 1181-1189.
Webb, B.A., Dosey, A.M., Wittmann, T., Kollman, J.M., and Barber, D.L. (2017). The glycolytic enzyme phosphofructokinase-1 assembles into filaments. The Journal of Cell Biology, 258, jcb.201701084-13.
Yalcin, A., Clem, B.F., Imbert-Fernandez, Y., Ozcan, S.C., Peker, S., Neal, J.O.A., Klarer, A.C., Clem, A.L., Telang, S., and Chesney, J. (2014). 6-Phosphofructo-2-kinase (PFKFB3) promotes cell cycle progression and suppresses apoptosis via Cdk1-mediated phosphorylation of p27. Cell Death and Disease, 5, e1337. doi: 10.1038/cddis.2014.292.
Yu, B., Lane, M.E., and Wadler, S. (2002). SU9516, a cyclin-dependent kinase 2 inhibitor, promotes accumulation of high molecular weight E2F complexes in human colon carcinoma cells. Biochemical Pharmacology, 64, 1091-1100.
Schmitt, Danielle L. (2017), Compartmentalization of Metabolic Pathways and Their Influence on Cellular Energetics, Dissertation.
Schmitt, D.L., Dranchak, P., Inglese, J., An, S. (2017). Spatial Regulation of Enzyme Compartmentalization of Small Molecules in Live Cells. Poster Presentation, 10th Annual Frontiers at the Chemistry and Biology Interface Symposium, University of Delaware, Newark, DE, May 6, 2017.
Zanella, F., Lorens, J.B., and Link, W. (2010). High content screening: seeing is believing. Trends in Biotechnology, 28, 237-245.
Schmitt, Danielle L., et al.; "Spatial Organization of Metabolic Enzyme Complexes in Cells," Biochemistry, 2017, pp. 3184-3196, vol. 56, DOI: 10.1021/acs.biochem.7b00249.
Ali, S., Heathcote, D.A., Kroll, S.H.B., Jogalekar, A.S., Scheiper, B., Patel, H., Brackow, J., Siwicka, A., Fuchter, M.J., Periyasamy, M., et al. (2009). The development of a selective cyclin-dependent kinase inhibitor that shows antitumor activity. Cancer Research, 69, 6208-6215.
An, S., Kumar, R., Sheets, E.D., and Benkovic, S.J. (2008). Reversible compartmentalization of de novo purine biosynthetic complexes in living cells. Science, 320, 103-106.
Anastassiadis, T., Deacon, S.W., Devarajan, K., Ma, H., and Peterson, J.R. (2011). Comprehensive assay of kinase catalytic activity reveals features of kinase inhibitor selectivity Nature Biotechnology, 29, 1039-1045.
Anjum, R., and Blenis, J. (2008). The RSK family of kinases: emerging roles in cellular signalling. Nat Rev Mol Cell Biol, 9, 747-758.
Arai, K., Eguchi, T., Rahman, M.M., Sakamoto, R., Masuda, N., Nakatsura, T., Calderwood, S.K., Kozaki, K.-I., and Itoh, M. (2016). A Novel High-Throughput 3D Screening System for EMT Inhibitors: A Pilot Screening Discovered the EMT Inhibitory Activity of CDK2 Inhibitor SU9516. PLoS ONE, 11, e0162394-18.
Asghar, U., Witkiewicz, A.K., Turner, N.C., and Knudsen, E.S. (2015). The history and future of targeting cyclin-dependent kinases in cancer therapy. Nat Rev Drug Disc, 14, 130-146.
Bain, J., Plater, L., Elliott, M., Shpiro, N., Hastie, C.J., Mclauchlan, H., Klevernic, I., Arthur, J.S.C., Alessi, D.R., and Cohen, P. (2007). The selectivity of protein kinase inhibitors: a further update. Biochem. J., 408, 297-315.

Bensaad, K., Tsuruta, A., Selak, M.A., Vidal, M.N.C., Nakano, K., Bartrons, R., Gottlieb, E., and Vousden, K.H. (2006). TIGAR, a p53-Inducible Regulator of Glycolysis and Apoptosis. Cell 126, 107-120.
Bitterman, J.L., and Chung, J.H. (2014). Metabolic effects of resveratrol: addressing the controversies. Cell. Mol. Life Sci, 72, 1473-1488.
Borisa, A.C., and Bhatt, H.G. (2017). A comprehensive review on Aurora kinase: Small molecule inhibitors and clinical trial studies. European Journal of Medicinal Chemistry, 140, 1-19.
Carmena, M., and Earnshaw, W.C. (2003). The cellular geography of aurora kinases. Nat Rev Mol Cell Biol, 4, 842-854.
Chesney, J. (2006). 6-phosphofructo-2-kinase/fructose-2,6-bisphosphatase and tumor cell glycolysis. Curr Opin Clin Nutr Metab Care, 9, 535-539.
Chu, H., and Low, P.S. (2006). Mapping of glycolytic enzyme-binding sites on human erythrocyte band 3. Biochem. J., 100, 143-151.
Crowley, L.C., Chojnowski, G., and Waterhouse, N.J. (2016). Measuring the DNA Content of Cells in Apoptosis and at Different Cell-Cycle Stages by Propidium Iodide Staining and Flow Cytometry. Cold Spring Harb Protoc, 2016, pdb.prot087247.
Deprez, J., Vertommen, D., Alessi, D.R., Hue, L., and Rider, M.H. (1997). Phosphorylation and activation of heart 6-3hosphofructo-2-kinase by protein kinase B and other protein kinases of the insulin signaling cascades. J. Biol. Chem., 272, 17269-17275.
Doménech, E., Maestre, C., Esteban-Martínez, L., Partida, D., Pascual, R., Fernández-Miranda, G., Seco, E., Campos-Olivas, R., Pérez, M., Megias, D., et al. (2015). AMPK and PFKFB3 mediate glycolysis and survival in response to mitophagy during mitotic arrest. Nat Cell Biol, 17, 1304-1316.
Endicott, J.A., and Noble, M.E.M. (2013). Structural characterization of the cyclin-dependent protein kinase family. Biochem. Soc. Trans., 41, 1008-1016.
Fox, M.H. (1980). A model for the computer analysis of synchronous DNA distributions obtained by flow cytometry. Cytometry, 1, 71-77.
Fry, D.W., Harvey, P.J., Keller, P.R., Elliott, W.L., Meade, M., Trachet, E., Albassam, M., Zheng, X., Leopold, W.R., Pryer, N.K., et al. (2004). Specific inhibition of cyclin-dependent kinase 4/6 by PD 0332991 and associated antitumor activity in human tumor xenografts. Molecular Cancer Therapeutics, 3, 1427-1438.
Gomez, L.S., Zancan, P., Marcondes, M.C., Ramos-Santos, L., Meyer-Fernandes, J.R., Sola-Penna, M., and Da Silva, D. (2013). Resveratrol decreases breast cancer cell viability and glucose metabolism by inhibiting 6-ahosphofructo-1 -kinase. Biochimie, 95, 1336-1343.
Haney, S.A., LaPan, P., Pan, J., and Zhang, J. (2006). High-content screening moves to the front of the line. Drug Discovery Today, 11, 889-894.
Hauf, S., Cole, R.W., LaTerra, S., Zimmer, C., Schnapp, G., Walter, R., Heckel, A., van Meel, J., Rieder, C.L., and Peters, J.-M. (2003). The small molecule Hesperadin reveals a role for Aurora B in correcting kinetochore-microtubule attachment and in maintaining the spindle assembly checkpoint. The Journal of Cell Biology, 161, 281-294.
Hu, J.-W., Sun, P., Zhang, D.-X., Xiong, W.-J., and Mi, J. (2014). Hexokinase 2 regulates G1/S checkpoint through CDK2 in cancer-associated fibroblasts. Cellular Signalling, 26, 2210-2216.
Hydbring, P., Malumbres, M., and Sicinski, P. (2016). Non-canonical functions of cell cycle cyclins and cyclin-dependent kinases. Nature Publishing Group, 17, 280-292.
Inglese, J., Auld, D.S., Jadhav, A., Johnson, R.L., Simeonov, A., Yasgar, A., Zheng, W., and Austin, C.P. (2006). Quantitative high-throughput screening: a titration-based approach that efficiently identifies biological activities in large chemical libraries. Proc Natl Acad Sci USA, 103, 11473-11478.
Inglese, J., Johnson, R.L., Simeonov, A., Xia, M., Zheng, W., Austin, C.P., and Auld, D.S. (2007). High-throughput screening assays for the identification of chemical probes. Nat Chem Biol, 3, 466-479.
Jani, J.P., Arcari, J., Bernardo, V., Bhattacharya, S.K., Briere, D., Cohen, B.D., Coleman, K., Christensen, J.G., Emerson, E.O., Jakowski,

(56) References Cited

PUBLICATIONS

A., et al. (2010). PF-03814735, an Orally Bioavailable Small Molecule Aurora Kinase Inhibitor for Cancer Therapy. Molecular Cancer Therapeutics, 9, 883-894.

Jeon, M., Kang, H.-W., An, S. (2018) A Mathematical Model for Enzyme Clustering in Glucose Metabolism. Scientific Reports, 8, 2696.

Jin, M., Fuller, G.G., Han, T., Yao, Y., Alessi, A.F., Freeberg, M.A., Roach, N.P., Moresco, J.J., Kamovsky, A., Baba, M., et al. (2017). Glycolytic Enzymes Coalesce in G Bodies under Hypoxic Stress. Cell Reports, 20, 895-908.

Johnson, D.G., and Walker, C.L. (1999). Cyclins and cell cycle checkpoints. Annu. Rev. Pharmacol. Toxicol., 39, 295-312.

Kalucka, J., Missiaen, R., Georgiadou, M., Schoors, S., Lange, C., De Bock, K., Dewerchin, M., and Carmeliet, P. (2015). Metabolic control of the cell cycle. Cell Cycle, 14, 3379-3388.

Kaplon, J., van Dam, L., and Peeper, D. (2015). Two-way communication between the metabolic and cell cycle machineries: the molecular basis. Cell Cycle, 14, 2022-2032.

Kohnhorst, C.L., Kyoung, M., Jeon, M., Schmitt, D.L., Kennedy, E.L., Ramirez, J., Bracey, S.M., Luu, B.T., Russell, S. J., and An, S. (2017). Identification of a multienzyme complex for glucose metabolism in living cells. J. Biol. Chem., 292, 9191-9203.

Korn, K., and Krausz, E. (2007). Cell-based high-content screening of small-molecule libraries. Current Opinion in Chemical Biology, 11, 503-510.

Lane, M.E., Yu, B., Rice, A., Lipson, K.E., Liang, C., Sun, L., Tang, C., McMahon, G., Pestell, R.G., and Wadler, S. (2001). A novel cdk2-selective inhibitor, SU9516, induces apoptosis in colon carcinoma cells. Cancer Research, 61, 6170-6177.

Lee, W.-H., Choi, J.-S., Byun, M.-R., Koo, K.-T., Shin, S., Lee, S.-K., and Surh, Y.-J. (2010). Functional inactivation of triosephosphate isomerase through phosphorylation during etoposide-induced apoptosis in HeLa cells: Potential role of Cdk2. Toxicology, 278, 224-228.

Liu, L.L., Long, Z.J., Wang, L.X., Zheng, F.M., Fang, Z.G., Yan, M., Xu, D.F., Chen, J.J., Wang, S.W., Lin, D.J., et al. (2013). Inhibition of mTOR Pathway Sensitizes Acute Myeloid Leukemia Cells to Aurora Inhibitors by Suppression of Glycolytic Metabolism. Molecular Cancer Research, 11, 1326-1336.

Michael, S., Auld, D., Klumpp, C., Jadhav, A., Zheng, W., Thorne, N., Austin, C.P., Inglese, J., and Simeonov, A. (2008). A Robotic Platform for Quantitative High-Throughput Screening. ASSAY and Drug Development Technologies, 6, 637-657.

Mor, I., Cheung, E.C., and Vousden, K.H. (2011). Control of glycolysis through regulation of PFK1: old friends and recent additions. Cold Spring Harb. Symp. Quant. Biol., 76, 211-216.

Morgan, D.O. (1997). Cyclin-dependent kinases: engines, clocks, and microprocessors. Annu. Rev. Cell Dev. Biol., 13, 261-291.

Moshinsky, D.J., Bellamacina, C.R., Boisvert, D.C., Huang, P., Hui, T., Jancarik, J., Kim, S.-H., and Rice, A.G. (2003). SU9516: biochemical analysis of cdk inhibition and crystal structure in complex with cdk2. Biochemical and Biophysical Research Communications, 310, 1026-1031.

Nierode, G., Kwon, P.S., Dordick, U.S., and Kwon, S.-J. (2016). Cell-Based Assay Design for High-Content Screening of Drug Candidates. Journal of Microbiology and Biotechnology, 26, 213-225.

Nomanbhoy, T.K., Sharma, G., Brown, H., Wu, J., Aban, A., Vogeti, S., Alemayehu, S., Sykes, M., Rosenblum, J.S., and Kozarich, J.W. (2016a). Chemoproteomic Evaluation of Target Engagement by the Cyclin-Dependent Kinase 4 and 6 Inhibitor Palbociclib Correlates with Cancer Cell Response. Biochemistry, 55, 5434-5441.

Roy, D., Sheng, G.Y., Herve, S., Carvalho, E., Mahanty, A., Yuan, S., and Sun, L. (2017). Interplay between cancer cell cycle and metabolism: Challenges, targets and therapeutic opportunities. Biomed. Pharmacother, 89, 288-296.

Salazar-Roa, M., and Malumbres, M. (2017). Fueling the Cell Division Cycle. Trends in Cell Biology, 27, 69-81.

Sarathy, A., Wuebbles, R.D., Fontelonga, T.M., Tarchione, A.R., Griner, L.A.M., Heredia, D.J., Nunes, A.M., Duan, S., Brewer, P.D., Van Ry, T., et al. (2017). SU9516 Increases $\alpha7\beta1$ Integrin and Ameliorates Disease Progression in the mdx Mouse Model of Duchenne Muscular Dystrophy. Molecular Therapy, 25(6), 1395-1407.

Zhang, J., Chung, T., and Oldenburg, K. (1999). A Simple Statistical Parameter for Use in Evaluation and Validation of High Throughput Screening Assays. Journal of Biomolecular Screening, 4, 67-73.

METHOD OF IDENTIFYING A COMPOUND WHICH AFFECTS THE MULTIENZYME METABOLIC ASSEMBLY OF GLUCOSE METABOLISM AND ITS ASSOCIATION WITH CELL CYCLE PROGRESSION IN CANCER CELLS

CROSS REFERENCE TO RELATED APPLICATIONS

This application is filed under the provisions of 35 U.S.C. § 111(a) and claims priority to U.S. Provisional Patent Application No. 62/690,027 filed on Jun. 26, 2018 in the name of Songon An, et al. and entitled "High Content Screening Identifies the Association of the Cell Cycle with the Multienzyme Metabolic Assembly of Glucose Metabolism," which is hereby incorporated by reference herein in its entirety.

STATEMENT REGARDING FEDERALLY SPONSORED RESEARCH

Portions of this invention may have been financially supported by the United States Government support under a grant from the National Institutes of Health/National Institute of General Medical Sciences (NIH/NIGMS) under Grant Number R01-GM125981 and Grant Number T32-GM066706.

FIELD

The present invention relates to a cell-based qHTS assay and process of using same to identify compounds which induce the assembly of a multienzyme complex, and which affects the cell cycle progression, in a cancer cell.

BACKGROUND OF THE INVENTION

The enzymes in glycolysis in a variety of species have been proposed to form a multienzyme complex in the cell (Schmitt and An, 2017). In particular, glycolytic enzymes in human erythrocytes have been shown to colocalize on the inner cell membrane with membrane-bound protein band 3 (Chu and Low, 2006). In addition, it is known that human liver-type phosphofructokinase 1 (PFK1) forms cytoplasmic clusters in several human cancer cells by recruiting other rate-limiting enzymes in glycolysis and gluconeogenesis, forming a multienzyme metabolic assembly, namely the "glucosome" (Kohnhorst et al., 2017). It appears that the enzymes in glucose metabolism are spatially organized into cytoplasmic clusters in human cells.

Glucose metabolism has also been shown to oscillate throughout the cell cycle of mammalian cells (Kalucka et al., 2015). In particular, the expression level and activity of phosphofructokinase-2/fructose-2,6-bisphosphatase (PFKFB3) significantly increases during the G1/S transition, which in turn activates PFK1 in glycolysis for metabolic oscillation of the cell (Kaplon et al., 2015; Salazar-Roa and Malumbres, 2017). Then, glycolysis is downregulated in the S phase of the cell cycle due to the degradation of PFKFB3. Subsequently, nucleotide biosynthesis and the pentose phosphate pathway follow the oscillation of glycolysis in a delayed fashion (Kaplon et al., 2015). Therefore, glycolytic demand is intricately regulated throughout the G1/S phase of the cell cycle.

It is important to mention that the cell cycle is regulated by a well-orchestrated mechanism that involves cyclin dependent kinases (CDKs), their associated cyclins, and several transcription factors (Hydbring et al., 2016; Salazar-Roa and Malumbres, 2017; Yalcin et al., 2014). In particular, during the G1 phase, the association of CDK4 and CDK6 with cyclin D is important for cell cycle progression. The interaction of CDK2 with cyclin E is also needed for progression through the G1 phase while the CDK2-cyclin A interaction is needed for the G1/S phase transition (Johnson and Walker, 1999; Morgan, 1997). These CDK/cyclin interactions play an essential role in regulating cell cycle checkpoints, gene expression, and other processes essential to a dividing cell.

Meanwhile, cell-based high-content and high-throughput screening assays have been advantageous for understanding regulatory mechanisms of cellular processes in human cells (Haney et al., 2006; Zanella et al., 2010). Traditional high throughput screening methods use small molecule libraries at single concentrations, which have a higher probability of missing biologically relevant phenotypes during the screening (Inglese et al., 2006; Michael et al., 2008). Accordingly, quantitative high throughput screening (qHTS) methods have been developed to screen small molecule libraries in a multi-point titration, producing concentration-response curves per small molecule in the libraries for evaluation (Inglese et al., 2006). Current qHTS assays have been successfully employed when cell-based assays report protein translocation to or from cellular compartments (Korn and Krausz, 2007), or changes of protein expression levels (Nierode et al., 2016). Hence, cellular mechanisms that regulate the reversible compartmentalization of human enzymes involved in glucose metabolism can be systematically dissected by employing the qHTS technique.

There is a need for a cell-based qHTS assay to monitor the formation of PFK1 clusters by the action of small molecules to identify small molecules that promote intracellular PFK1 clustering in a cell cycle-dependent manner.

SUMMARY OF THE INVENTION

In a first aspect, an assay method to identify an active testing compound which induces clustering in a host cell is described, the method comprising:
  providing a medium comprising host cells that express phosphofructokinase 1 (PFK1) fused to a fluorescent protein (PFK1-FP);
  introducing at least two concentrations of a testing compound into individual aliquots of the medium and incubating same;
  imaging the host cells of the incubated medium to identify testing compounds inducing clusters having at least a minimum area and sensitivity; and
  plotting a quantitative high-throughput screening (qHTS) titration curve of the percent of host cells showing PFK1-FP clustering versus the log compound concentration for the testing compound,
  wherein the qHTS titration curve of the testing compound includes the titration curve of a positive control compound, wherein the testing compound is considered active when the qHTS titration curve is a full titration curve or a partial titration curve.

In a second aspect, the present application relates to a method of identifying a testing compound which affects cell cycle progression in a host cell, the method comprising:
  providing a medium comprising host cells that express phosphofructokinase 1 (PFK1) fused to a fluorescent protein (PFK1-FP);

introducing at least two concentrations of a testing compound into individual aliquots of the medium and incubating same;

imaging the host cells of the incubated medium to identify testing compounds inducing clusters having at least a minimum area and sensitivity; and plotting a quantitative high-throughput screening (qHTS) titration curve of the percent of host cells showing PFK1-FP clustering versus the log compound concentration for the testing compound, wherein the qHTS titration curve of the testing compound includes the titration curve of a positive control compound, wherein the testing compound affects cell cycle progression when the qHTS titration curve is a full titration curve or a partial titration curve.

Other aspects, features and embodiments of the invention will be more fully apparent from the ensuing disclosure and appended claims.

DETAILED DESCRIPTION, AND PREFERRED EMBODIMENTS THEREOF

Figure 1B:
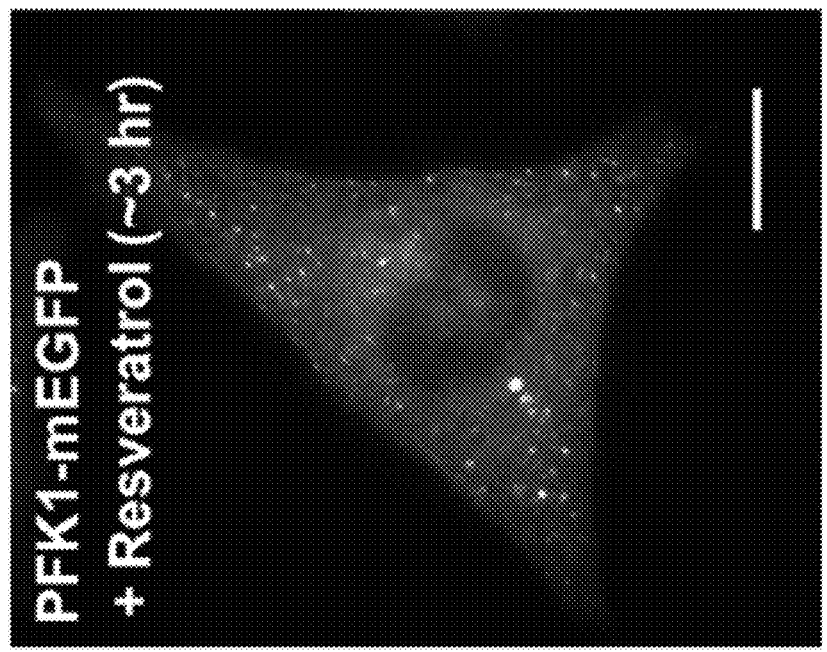
FIG. 1B is an image of resveratrol-induced clustering of PFK1-mEGFP in fixed HeLa-T-PFK1G cells. Cells were treated with 200-250 μM resveratrol for three hours. Scale bar, 10 μm.

The present inventors previously investigated the spatial organization of metabolic enzymes participating in glucose metabolism in human cells, providing evidence that PFK1 forms various sizes of cytoplasmic clusters in human cancer cells, independent of protein expression levels and of the choice of fluorescent tags (Kohnhorst et al., 2017, which is hereby incorporated herein in its entirety). It was further shown that PFK1 colocalizes with other cytoplasmic rate-limiting enzymes of the pathway, including human liver-type fructose-1,6-bisphosphatase (FBPase), pyruvate kinase M2 (PKM2), and phosphoenolpyruvate carboxykinase 1 (PEPCK1), evidencing the formation of a multienzyme complex, namely the glucosome. It is known that the size of glucosome clusters becomes larger in human breast carcinoma cells (Hs578T), relative to non-cancerous human breast tissue cells (Hs578Bst), demonstrating the spatial alteration of glucose metabolism in cancer cells (Id.).

A reporter system was developed for glucosome formation using doxycycline to induce expression of PFK1 with a monomeric form of enhanced green fluorescent protein (PFK1-mEGFP) in HeLa TetOn cells (Schmitt et al., 2017). In initial studies, small molecules were found to induce the clustering of PFK1-mEGFP (Id.). In addition, an algorithm was optimized for detecting PFK1-mEGFP clustering in whole cells (Id.).

Using the previous discoveries of their own laboratory, the present inventors have developed a quantitative high-content high-throughput screening assay using HeLa Tet-On cells that stably express PFK1-mEGFP. The spatial assembly of PFK1-mEGFP at single cell levels is monitored as an intracellular readout for the glucosome assembly in a high-throughput fashion. The cell-based qHTS assay can be used to monitor the formation of PFK1-mEGFP clusters by the action of small molecules and to identify small molecules that promote intracellular PFK1 clustering in a cell cycle-dependent manner. Small molecules that promote intracellular PFK1-mEGFP clustering during the assay are considered "active" and are strong candidates for apoptosis induction, thus permitting the rapid identification of compounds that may be used to treat cancer.

As used herein, the term "small molecule" and analogous terms include, but are not limited to, peptides, peptidomimetics, amino acids, amino acid analogs, polynucleotides, polynucleotide analogs, nucleotides, nucleotide analogs, organic or inorganic compounds (i.e., including heterorganic and/or organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, "cancer" relates to the physiological condition that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatome, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

As used herein, the term "fluorescent protein" refers to a polypeptide with the capacity to emit light in response to the absorption of light or other electromagnetic radiation. Non-limiting illustrative examples of fluorescent proteins are green fluorescent protein (GFP or wtGFP), GFP variants for different emission wavelengths, emission intensity and/or protein stability such as Superfolder GFP, monomeric form of enhanced GFP (mEGFP), EGFP variants for different emission wavelengths (colors) such as blue fluorescent protein (EBFP), cyan fluorescent protein (ECFP), and yellow fluorescent protein (YFP), GFPuv (characterized by having mutations F99S, M153T and V163A in the GFP sequence), Emerald, mPlum, mCherry, tdTomato, mStrawberry, J-Red, mOrange, mKO, YFP, EYFP, mCitrine, Venus, YPet, CyPet, CFP, ECFP, mCFPm, Cerulean, and T-Sapphire. Other fluorescent polypeptides include red fluorescent protein (RFP), DsRed and variants thereof, DsRed2, DsRed-Express, RedStar, HcRed1, Kaede, EosFP, and Kindling fluorescent protein (KFP). In a particular embodiment, the fluorescent protein is green fluorescent protein, more preferably mEGFP.

As used herein, the term "green fluorescent protein" or "GFP" refers to a protein consisting of 239 amino acids with a molecular weight of 26.9 kDa and showing bright green fluorescence when exposed to blue ultraviolet light. Although many other marine organisms have similar green fluorescent proteins, GFP traditionally refers to the first protein isolated from jellyfish *Aequorea victoria*. *A. victoria* GFP has a major excitation maximum at a wavelength of 395 nm and a minor one at 475 nm. The emission maximum thereof is at 509 nm. The fluorescence quantum yield of GFP is 0.79.

As defined herein, small clusters are about 0.1 $\mu m^2$, medium clusters are greater than 0.1 $\mu m^2$ to less than about 3 $\mu m^2$, and large clusters are greater than about 3 $\mu m^2$ to less than about 8 $\mu m^2$.

In a first aspect, an assay method to identify an active testing compound which induces clustering in a host cell is described, the method comprising:
  providing a medium comprising host cells that express phosphofructokinase 1 (PFK1) fused to a fluorescent protein (PFK1-FP);
  introducing at least two concentrations of a testing compound into individual aliquots of the medium and incubating same;
  imaging the host cells of the incubated medium to identify testing compounds inducing clusters having at least a minimum area and sensitivity; and
  plotting a quantitative high-throughput screening (qHTS) titration curve of the percent of host cells showing PFK1-FP clustering versus the log compound concentration for the testing compound,
  wherein the qHTS titration curve of the testing compound includes the titration curve of a positive control compound, wherein the testing compound is considered active when the qHTS titration curve is a full titration curve or a partial titration curve.

In one embodiment, the assay method to identify an active testing compound which induces clustering in a host cell comprises:
  providing a medium comprising host cells that express phosphofructokinase 1 (PFK1) fused to a monomeric form of enhanced green fluorescent protein (PFK1-mEGFP);
  introducing at least two concentrations of a testing compound into individual aliquots of the medium and incubating same;

imaging the host cells of the incubated medium to identify testing compounds inducing clusters having at least a minimum area and sensitivity; and plotting a quantitative high-throughput screening (qHTS) titration curve of the percent of host cells showing PFK1-mEGFP clustering versus the log compound concentration for the testing compound, wherein the qHTS titration curve of the testing compound includes the titration curve of a positive control compound, wherein the testing compound is considered active when the qHTS titration curve is a full titration curve or a partial titration curve.

In a second aspect, the present application relates to a method of identifying a testing compound which affects cell cycle progression in a host cell, the method comprising:

providing a medium comprising host cells that express phosphofructokinase 1 (PFK1) fused to a fluorescent protein (PFK1-FP);

introducing at least two concentrations of a testing compound into individual aliquots of the medium and incubating same;

imaging the host cells of the incubated medium to identify testing compounds inducing clusters having at least a minimum area and sensitivity; and plotting a quantitative high-throughput screening (qHTS) titration curve of the percent of host cells showing PFK1-FP clustering versus the log compound concentration for the testing compound, wherein the qHTS titration curve of the testing compound includes the titration curve of a positive control compound, wherein the testing compound affects cell cycle progression when the qHTS titration curve is a full titration curve or a partial titration curve.

In an embodiment of the second aspect, a method of identifying a testing compound which affects cell cycle progression in a host cell comprises:

providing a medium comprising host cells that express phosphofructokinase 1 (PFK1) fused to a monomeric form of enhanced green fluorescent protein (PFK1-mEGFP);

introducing at least two concentrations of a testing compound into individual aliquots of the medium and incubating same;

imaging the host cells of the incubated medium to identify testing compounds inducing clusters having at least a minimum area and sensitivity; and plotting a quantitative high-throughput screening (qHTS) titration curve of the percent of host cells showing PFK1-mEGFP clustering versus the log compound concentration for the testing compound, wherein the qHTS titration curve of the testing compound includes the titration curve of a positive control compound, wherein the testing compound affects cell cycle progression when the qHTS titration curve is a full titration curve or a partial titration curve.

In one embodiment, PFK1-mEGFP is transfected into HeLa Tet-On 3G host cells followed by incubation with doxycycline for an effective time, for example about 24 hr, to trigger the expression of PFK1-mEGFP in the HeLa Tet-On 3G stably transfected cell line (hereinafter "HeLa-T-PFK1G cells"). The HeLa-T-PFK1G cells are plated in microtiter plates, for example a 6, 12, 24, 48, 96, 384 or 1536 well plates, and a volume of each testing compound or a positive control compound that is known to promote clustering of PFK1-mEGFP at dilution are added to respective wells comprising the HeLa-T-PFK1G cells and incubated for an effective time. In a preferred embodiment, the dilution is in a range from about 50-fold to 300-fold, preferably about 150-fold to about 250-fold, more preferably about 200-fold. Positive control compounds can include, but are not limited to, resveratrol, SU9516, kenpaullone, or olomoucine. The concentration of positive control compound used to induce clustering can be in a range from about 50 µM to about 500 µM, preferably about 200 µM to about 250 µM for resveratrol and 57.5 µM for each of SU9516, kenpaullone, and olomoucine. The density of HeLa-T-PFK1G cells per well is about 100 cells/well to about 1000 cells/well depending on well density of plate, preferably about 400 cells/well in 1536-well format. Following fixing, staining, and washing, the cells were imaged, using techniques and high-content analyzers capable of reading microtiter plates. Well images were analyzed with imaging software to quantify phenotypic responses characterized by PFK1-mEGFP clustering within the cytoplasm of the cells. A titration-response curve per compound tested, including the curve for the positive control compound, is plotted as the percent of cells showing PFK1-mEGFP clusters against the log concentration of compound (3.7 nM-57.5 µM final concentration range for most test compounds). Algorithm-based software can be used to interpret the curves to identify those that are suggestive of an active testing compound (i.e., increased PFK1-mEGFP clustering in response to increased compound concentrations) (Inglese, 2006). Preferred curves include those of class 1 (full titration) or class 2 (partial titration or bell curve). This quantitative high-throughput screening (qHTS) assay can be used to screen libraries consisting of thousands of small molecules in full titration spanning several log order magnitude concentration range effectively and efficiently to identify active molecules.

It should be appreciated that the host cells described in the instant application are HeLa Tet-On 3G host cells but the inventions disclosed herein are not intended to be limited to same. For example, a number of mammalian cell lines are known in the art and include immortalized cell lines available from the American Type Culture Collection (ATCC), including, but not limited to, Chinese hamster ovary (CHO) cells, HeLa cells, HEK293, baby hamster kidney (BHK) cells, monkey kidney cells (COS), human hepatocellular carcinoma cells (e.g., Hep G2), human mammary gland/breast carcinoma cells (e.g., Hs 578T), Madin-Darby bovine kidney ("MDBK") cells, and NOS cells derived from carcinoma cells, such as sarcoma. Alternatively, the host cells can be the harvested cells from a mammal, for example a human, so that targeted testing compounds can be identified for a specific individual for personalized medicine. For example, the harvested cells can be cancerous so that a testing compound can be identified that causes clustering and hence may affect the cell cycle progression of the individual's cells. The person skilled in the art will readily understand how to harvest cells from a specific individual for use as the host cell.

Advantageously, the testing compound that induces PFK1-mEGFP clusters, i.e., affects the cell cycle progression in a cell, may be used to treat cancer because of the ability of the testing compound to induce apoptosis. In other words, the method and assay described herein relates to a cell-based qHTS assay that can be used to identify new compounds, whether naturally occurring, already synthesized, or to be discovered or synthesized in the future, that may be used to treat cancer.

Another advantage of the presently described assay and method of using same is that a positive control compound such as resveratrol can be used to identify a testing compound that can induce clustering of PFK1-mEGFP in the host cell. Once said testing compound is identified, it can be used in a second cell-based qHTS assay as the established molecular target to determine what additional testing compounds, if any, are off-targets of the established molecular target. For example, using the reporter system for glucosome formation, wherein doxycycline is used to induce expression of PFK1-mEGFP in HeLa TetOn cells, and resveratrol was the positive control compound, an initial screen monitoring the formation of the enzyme assembly identified one hit compound (i.e., SU9516) from the Library of Pharmacologically Active Compounds (LOPAC). SU9516 has been known to be a cell cycle regulator (see, example below). A subsequent screen using the Library of Kinase Inhibitors (LOKI), and SU9516 as the molecular target (i.e., positive control compound), further disclosed specific protein kinases as key regulators of PFK1-mEGFP clustering in the cells, wherein said specific protein kinases are primarily involved in the cell cycle progression (see, example below).

In another aspect, a method of analyzing cell cycle progression, said method comprising:
  providing a medium comprising host cells that express phosphofructokinase 1 (PFK1) fused to a fluorescent protein (PFK1-FP);
  introducing the testing compound into the medium;
  harvesting the cells;
  analyzing the expression of PFK1-FP in the cells using flow cytometry; and
  calculating each phase of the cell cycle progression using algorithm-based software,
  wherein the induction of PFK1-FP clusters in the host cell is indicative of changes in cell populations in different phases of the cell cycle.

For example, without limiting same, the analysis and calculation can be performed using FlowJo (FlowJo, LLC), wherein cell populations are gated based on the expression of PFK1-mEGFP clusters in cells as well as their size and granularity. The cell cycle progression can assessed by the Dean-Jett-Fox analysis using Cell Cycle platform available in FlowJo. Other flow cytometers and algorithms for analyzing the data are known in the art.

In one embodiment, the method of analyzing cell cycle progression comprises:
  providing a medium comprising host cells that express phosphofructokinase 1 (PFK1) fused to a monomeric form of enhanced green fluorescent protein (PFK1-mEGFP);
  introducing the testing compound into the medium;
  harvesting the cells;
  analyzing the expression of PFK1-mEGFP in the cells using flow cytometry; and
  calculating each phase of the cell cycle progression using a mathematical algorithm,
  wherein the induction of PFK1-mEGFP clusters in the host cell is indicative of changes in cell populations in different phases of the cell cycle.

Without being bound by theory, the results suggest that PFK1-mEGFP clusters are spatiotemporally regulated by the cell cycle in human cancer cells, thus indicating a functional association of the cell cycle with the enzyme assembly in glucose metabolism, the glucosome.

The features and advantages of the invention are more fully illustrated by the following non-limiting examples, wherein all parts and percentages are by weight, unless otherwise expressly stated.

Example 1

Materials

A plasmid expressing PFK1 conjugated with a monomeric enhanced green fluorescent protein (mEGFP) was prepared previously (Kohnhorst et al., 2017). Note that the mEGFP used contains three point mutations, A206K, L221K, and F223R, which prevent oligomerization of EGFP in cells (An et al., 2008). Small molecules used were dissolved in DMSO (Sigma) and used at the concentrations indicated. The small molecules include resveratrol (Sigma), clemastine fumarate (Sigma), ARP101 (Tocris), 1,10-phenanthroline (Acros Organics), Triflupromazine hydrochloride (Sigma), Kenpaullone (Sigma), calmidazolium chloride (Sigma), PAC-1 (Sigma), and SU9516 (Tocris).

Generation of Stably Transfected HeLa-T-PFK1-mEGFP Cell Line

The HeLa-T-PFK1-mEGFP stable cell line (hereafter, HeLa-T-PFK1G) was successfully generated using the HeLa Tet-On® 3G inducible expression system (Clontech) according to the manufacturer's protocol. Briefly, the cDNA of PFK1-mEGFP was amplified by PCR and cloned into the pTRE3G vector (Clontech). The pTRE3G vector containing PFK1-mEGFP was then co-transfected into HeLa Tet-On 3G cells (Clontech) along with the linear selection marker of hygromycin using Xfect (Clontech). These cells were cultured in a medium containing 200 µg/mL G418 sulfate (Santa Cruz Biotechnology). After stabilizing and splitting confluent cells, clonal selection was begun by introducing 100 µg/mL hygromycin B (Invitrogen). Cells were monitored daily, and the medium was exchanged until the formation of drug-resistant colonies was observed. Isogenic harvesting of the colonies was achieved by using sterilized cloning disks saturated with a Trypsin:EDTA solution (Corning, Cat#25-053-C1) to gently remove colonies from the cell culture plate and seed them in the fresh medium. Colonies were screened for PFK1-mEGFP expression in both the absence and presence of 1 µg/mL doxycycline under fluorescence microscopy. The colony with the highest expression level (i.e., brightest mEGFP fluorescence) was selected. Subsequently, the stable cell line, referred to as HeLa-T-PFK1G, was validated as having a reproducible expression efficiency of ~85-90% of the cell population upon the induction with doxycycline. HeLa-T-PFK1G cells were maintained in Roswell Park Memorial Institute 1640 (RPMI 1640, Mediatech Cat#10-040-CV) or Dulbecco's Modified Eagle Medium (DMEM with high glucose, Gibco Cat#11965-092) supplemented with 10% dialyzed fetal bovine serum (FBS, Atlanta Biologicals, 12-14 MWCO, Cat #S12850) under the antibiotic selection, 200 µg/mL G418 sulfate (Santa Cruz Biotechnology) and 100 µg/mL hygromycin B (Invitrogen), along with either 50 µg/mL gentamycin sulfate (Corning) or 1% penicillin-streptomycin (Gibco) for maintenance.

Other Cell Culture

Wild-type HeLa cells were acquired from the American Tissue Culture Collection (ATCC, Manassas, Va.) and maintained in RPMI 1640 supplemented with 10% dialyzed FBS and 50 µg/mL gentamycin sulfate in a HeraCell $CO_2$ incubator (37° C., 5% $CO_2$, and 95% humidity).

Transient Transfection

A day before transient transfection, wild-type HeLa cells were plated on either glass-bottomed 35 mm petri dishes (MatTek) or 8-well chambers (LabTek) in RPMI 1640 supplemented with 10% dialyzed FBS without antibiotics. The following day, HeLa cells were transfected with PFK1-mEGFP using Lipofectamine 2000 (Invitrogen Cat#11668019) in Opti-MEM I (ThermoFisher Cat#11058-021) and allowed to incubate in a HeraCell $CO_2$ incubator (37° C., 5% $CO_2$, and 95% humidity). Approximately 5 hours later, the medium was exchanged for fresh growth medium and incubated overnight in the $CO_2$ incubator.

High-Resolution Fluorescence Live-Cell Imaging

A day before imaging, HeLa-T-PFK1G cells in RPMI1640 supplemented with 10% dialyzed FBS, 200 ug/ml G418 sulfate and 100 ug/ml hygromycin B, were plated in the presence of 1 μg/mL doxycycline to induce the expression of PFK1-mEGFP. On the day of imaging, the cells were washed three times with an imaging solution (20 mM HEPES (pH 7.4), 135 mM NaCl, 5 mM KCl, 1 mM $MgCl_2$, 1.8 mM $CaCl_2$) and 5.6 mM glucose) and allowed to adjust to ambient temperature for ~45-60 minutes prior to small molecule treatments. Meanwhile, transiently transfected HeLa cells were imaged after being washed with the imaging solution after ~24 hours following transfection. The cells were then treated with small molecules and incubated at 37° C. for the given time. All samples were imaged at ambient temperature (~25° C.) with a 60×1.45 NA objective lens (Nikon CFI Plan Apo TIRF) using a Photometrics CoolSnap EZ monochrome CCD camera on a Nikon Eclipse Ti-inverted C2 confocal microscope.

Epifluorescence imaging was carried out using a set of Z488/10-FC cleanup, HC TIRF Dichroic and 525/50-HC emission filter from Chroma Technology. Images were acquired using NIS Elements (Nikon) and images were analyzed using an ImageJ freeware (National Institutes of Health).

Compound Libraries

The assay was screened against two sets of chemical libraries that the National Center for Advancing Translational Sciences (NCATS) acquired: i) The library of pharmacologically active compounds (LOPAC, 1280 compounds, Sigma-Aldrich), and ii) the libraries of kinase inhibitors (LOKI, total 2958 compounds) that are composed of the published kinase inhibitor set (1108 compounds) and the mechanism interrogation plate collection (1850 compounds). Library preparation and management were performed as previously described (Yasgar A, et al., 2008—Compound Management for Quantitative High-Throughput Screening). Briefly, compounds were plated into 384-well plates (Greiner Bio-One) comprising a 11-point intra-plate titration with a serial dilution of 1:3 in DMSO ranging from 10 mM to 169 nM. Plates were reformatted in quadrants into 1536-well format using an Evolution P3 system (PerkinElmer).

Quantitative High-Content High-Throughput Screening (qHTS) Assay

HeLa-T-PFK1G cells were plated in 1536-well black, clear bottom, low base microwell plates (Aurora Microplates, Inc.) at a density of 400 cells/well in DMEM supplemented with 10% dialyzed FBS, 1% Pen-Strep, and 1 μg/mL doxycycline. The cells were incubated at 37° C., 5% $CO_2$, and 95% humidity for 16 hours. A qHTS assay was scaled to 4 μL volumes in 1536-well format in a semi-automated manner.

First, the qHTS assay was carried out with the LOPAC library (Sigma, 6.6 mM-10 mM, 7-point 1:3 inter-plate titration). To treat the cells with compounds in the library, 23 nL of each compound were transferred by a pintool (Kalypsys). The plates were then incubated overnight. The following day, resveratrol was dispensed at a final concentration of 200-250 μM using a Mosquito Dispenser (TTP Labtech) as a positive control to promote the clustering of PFK1-mEGFP in the cells. The plates were then incubated at room temperature for four hours.

Thereafter, the cells were fixed with 3.5% paraformaldehyde and nuclei were stained with a 1:1000 dilution of Hoechst dye (Invitrogen) for ~20 minutes. Cells were washed twice with 1×PBS with an EL406 microplate washer-dispenser (BioTek Instruments) and imaged using an INCell Analyzer 2000 (GE Healthcare Life Sciences) that was equipped with a Nikon 20× objective lens (Plan Fluor, NA=0.45, Elwb Corr Collar=0-2.0, CFI/60). Imaging of PFK1-mEGFP was done using the FITC channel (490/20x excitation, 525/36m emission) while imaging of the Hoechst dye was performed using the DAPI channel (350/50x excitation, 455/50m emission). Laser autofocus with offsets of 10.0 and 12.0 with 0.100 and 0.500 exposures respectively and 2×2 binning were used in a horizontal serpentine acquisition motion to collect one field of images from each well.

Second, the qHTS assay was carried out with the LOKI library (10 mM, 11-point 1:3 intra-plate titration). Again, 23 nL of compounds were transferred by a pintool (Kalypsys) in the final concentration range of 974 pM to 57.5 μM along with DMSO. Control compounds of SU9516, kenpaullone, and olomoucine, based on the LOPAC screening result, were used in an 8 point 1:3 titration (57.5 μM to 26.3 nM as final assay concentrations). The cells were then incubated overnight with small molecules. Approximately 24 hours later, the cells were fixed with 3.5% paraformaldehyde and nuclei were stained using a 1:1000 dilution of Hoechst dye for ~20 minutes. Cells were washed and imaged with an INCell Analyzer 2000 or INCell Analyzer 2200 (GE Healthcare Life Sciences) as described above.

Data Analysis of qHTS

Images were processed in the GE Workstation software and analyzed with a multitarget analysis of fluorescence. Top-hat segmentation of the DAPI channel was used to identify nuclei with a minimum area of 100 μm² and sensitivity of 40 settings. Multiscale top-hat segmentation of the FITC channel was used to identify cells with a characteristic area of 200 μm² and sensitivity of 70 settings. This allowed for the identification of fluorescent cells from the background or dead cells. Following cell segmentation, the same FITC channel was analyzed with multiscale top-hat segmentation to identify PFK1-mEGFP clusters with a size range of 0.2-2 μm², number scales of 1, process parameters of 1 pixel, sensitivity of 40, and inclusions in the cytoplasm. A filter of object area, that is, the area of PFK1-mEGFP clusters, below 30 μm² and an advanced sensitivity range of 1.5, was also applied. A decision tree thresholding was developed to identify cells with PFK1 clusters with three nodes. The start node required a cell intensity above 110 GL, the second node required a PFK1 cluster count above 1, and the third node required the total area of the PFK1 cluster above 5 μm². Ultimately, this allowed for the identification of cluster-positive cells over non-clustering cells. The total number of cells with a total area of PFK1 clusters above 5 μm² (most stringent parameter) and the total number of cells with any PFK1 clusters were calculated with the above algorithm and normalized by plate to the 57.5 μM kenpaullone intra-plate control as previously described (Inglese et al., 2006). Assay effectiveness including S:N (the signal to noise ratio) and Z' (the index of assay quality (Zhang et al., 1999)) were calculated for both parameters using the same respective control. Both parameters were normalized to the average signal of DMSO (vehicle)-treated wells as a zero percent neutral control and the average signal of 57.5 μM kenpaullone-treated wells as maximum PFK1-mEGFP clustering. Cell count based on the number of nuclei was used as a parameter of cytotoxicity, which was also normalized to the average signal of DMSO-treated wells as a zero percent neutral control and the average signal of 57.5 μM SU9516-treated wells as maximum PFK1-mEGFP clustering. The respective normalized data from each assay plate was corrected using DMSO only treated assay plates at the beginning and end of each library screen. In-house software (http://ncgc.nih.gov/pub/openhts/curvefit/) was used to fit the resulting intra-plate titration data to the standard Hill equation and concentration-response curves were classified by a titration curve as previously described (Southall et al.). Curve fits assignments of class 1.1, 1.2, 2.1 and 2.2s were considered active (i.e., promotion of the PFK1-mEGFP clusters) and visually confirmed. These classes included compounds which induced a full titration, a partial titration response, or a bell-shaped curve when PFK1-mEGFP clustering was plotted versus log compound concentration. These data for both PFK1 clustering parameters and cell count cytotoxicity were refit in GraphPad Prism (GraphPad Software, Inc.) with nonlinear regression log(compound) vs. response-variable slope (four parameters) fit. Bell-shaped curves were fit in GraphPad Prism with nonlinear regression and the equation of:

$$Y = S0 + \frac{(S1-S0)}{(1+10^{((EC50-X)*HillSlope1)})} + \frac{(S2-S1)}{(1+10^{((logIC50-X)*HillSlope2)})}$$

$EC_{50}$ were calculated using GraphPad Prism (GraphPad Software, Inc). In addition, raw image data from the wells treated with compounds that gave the active curve classes for either or both PFK1 clustering parameters and that were not categorized as cytotoxic by the curve class of cell count, were visually inspected in the GE workstation software to confirm the impact of compounds.

Cell Cycle Analysis

HeLa-T-PFK1G cells were plated in 6-well plates for a confluency of 70-90% in RPMI1640 supplemented with 10% dialyzed FBS in the presence of 1 ug/mL doxycycline. The following day, the cells were treated with SU9516 or DMSO for 24 hours. The cells were then harvested and analyzed for the cell cycle progression as previously described (Crowley et al., 2016). Briefly, hundreds of thousands of cells were removed from 6-well plates using trypsin, washed with 1×PBS (pH 7.4), resuspended in ice-cold PBS and fixed with ice-cold methanol for 20 minutes at 4° C. The cells were then washed and resuspended in the cell cycle buffer, which contains 30 ug/mL propidium iodide and 100 μg/mL RNase A (Thermo Cat # EN0531) in 1×PBS (pH 7.4). After being incubated for at least 45 minutes, flow cytometry was performed with a CyAn ADP (Beckman Coulter) running Summit V 4.00, equipped with a 488 nm laser line and 530/40 and 613/20 emission filters. Using FlowJo (FlowJo, LLC), cell populations were gated based on the expression of PFK1-mEGFP in cells as well as their size and granularity. The cell cycle progression was then assessed by the Dean-Jett-Fox analysis using Cell Cycle platform available in FlowJo (Fox, 1980).

Results

Development of a Cell-Based Assay for PFK1-mEGFP Clustering

The present inventors recently reported the propensity of PFK1-mEGFP to form varying sizes of spatial assemblies (i.e., clusters) in cancer cell lines (Kohnhorst et al., 2017). Specifically, in HeLa cells, 56±17% of cells have small-sized clusters (~0.1 μm$^2$), 20±8% of cells form medium-sized clusters (<3 μm$^2$), 20±5% of cells exhibit large-sized clusters (<8 μm$^2$) in the presence of medium-sized clusters, and 5±6% of cells show no clusters (see, FIG. 1A).

To develop a robust, cell-based assay for small molecule library screening, an inducible expression system was developed, wherein PFK1-mEGFP was expressed in HeLa Tet-On 3G cells (Clontech) upon incubation with 1 μg/mL doxycycline (Materials and Methods). Briefly, PFK1-mEGFP was stably transfected into HeLa Tet-On 3G cells. Treatment of 1 μg/mL doxycycline triggers the expression of PFK1-mEGFP in HeLa Tet-On 3G cells. Hereinafter, this stably transfected cell line is referred to as "HeLa-T-PFK1G" cells. This HeLa-T-PFK1G cell line was used for the qHTS assay development to find small molecules that promote the formation of PFK1-mEGFP clusters.

Figure 1A:
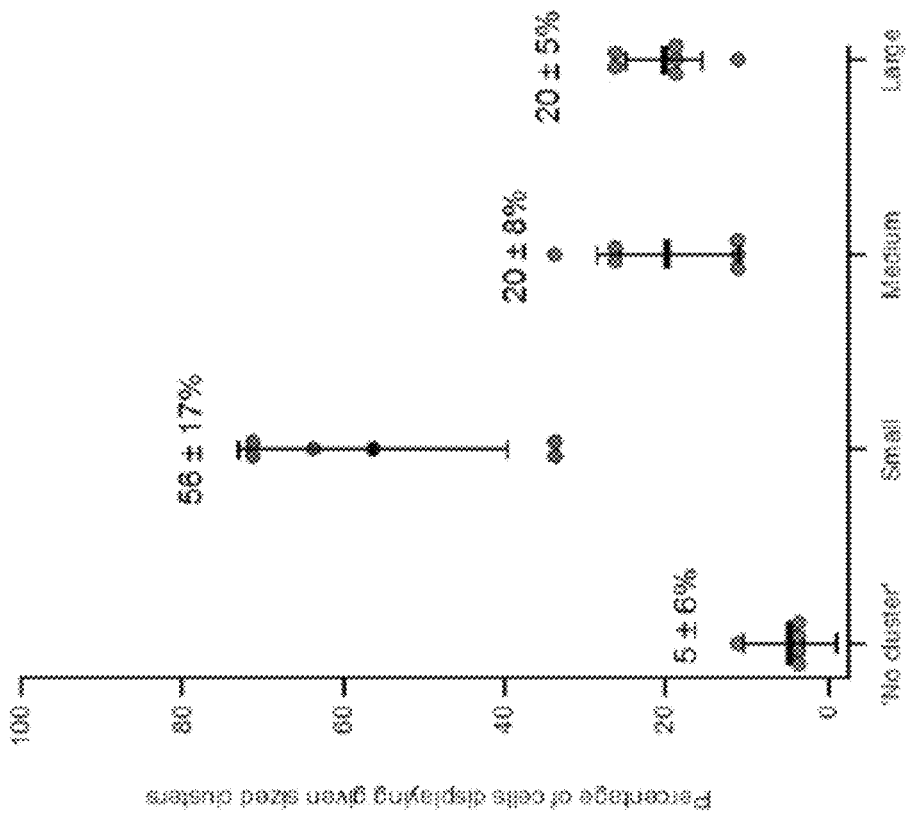
FIG. 1A illustrates the results of an analysis of clustering of transiently transfected PFK1-mEGFP in wild type HeLa cells, where small clusters ~0.1 $\mu m^2$, medium greater than 0.1 $\mu m^2$ to less than about 3 $\mu m^2$, and large greater than about 3 $\mu m^2$ to less than about 8 $\mu m^2$. Error bars represent the standard deviation of at least three trials.

Resveratrol was used to promote the formation of PFK1-mEGFP clusters in HeLa-T-PFK1G cells. Although mechanisms of action of resveratrol are not clear (Bitterman and Chung, 2014), resveratrol has been shown to have numerous effects on glycolysis (Gomez et al., 2013; Varoni et al., 2016). When PFK1-mEGFP expressing cells were treated with resveratrol (200-250 μM), approximately 80-90% of the cells exhibited medium- or large-sized clusters in the cytoplasm (FIG. 1B). Therefore, resveratrol was initially used as a positive control to develop an assay reporting PFK1-mEGFP clustering in HeLa-T-PFK1G cells.

Cell-Based qHTS with the LOPAC Library

To find new small molecules which induce PFK1 clustering, two repeats of qHTS using the LOPAC library were initially performed. HeLa-T-PFK1G cells were assayed against the library in a 7-fold titration (Materials and Methods) as described previously (Inglese et al., 2006). A titration-response curve per compound was then plotted with the percent of cells showing PFK1-mEGFP clusters versus the log compound concentration. Corresponding curve classes were subsequently assigned (Inglese et al., 2007). A curve class of 1 includes compounds that demonstrated a full titration curve, a curve class of 2 includes those that demonstrated a partial titration curve or a bell shaped curve, a curve class of 3 includes compounds that induced PFK1-mEGFP at only at a few concentrations, and compounds that had no effect or gave inconclusive results were assigned a curve class of 4 or 5. Consequently, 16 hit compounds from the LOPAC library (1.25% of the library) were repeatedly identified as promoting to some extent PFK1-mEGFP clustering in HeLa-T-PFK1G cells.

Subsequently, a validation screen was performed using these 16 compounds in a 10-point 1:3 titration. The final concentrations ranged from 57.5 μM to 8.7 nM. Images collected from wells treated with higher concentrations of the compounds were manually inspected for PFK1-mEGFP clustering rather than relying on the semi-automated decision process. Consequently, the number of hit compounds was reduced to 8 compounds (0.63% of the library) based on the ability to induce PFK1-mEGFP clustering (see, Table 1).

TABLE 1

Hit compounds from the LOPAC screen.

| NCGC ID | Compound Name |
| --- | --- |
| NCGC00167785-02 | PAC-1 |
| NCGC00015582-06 | Kenpaullone |
| NCGC00186031-01 | Arp 101 |
| NCGC00015233-04 | Calmidazolium chloride |
| NCGC00013043-08 | 1,10-phenanthroline |

TABLE 1-continued

Hit compounds from the LOPAC screen.

| NCGC ID | Compound Name |
|---|---|
| NCGC00015281-03 | Clemastine fumarate |
| NCGC00016012-09 | Triflupromazine |
| NCGC00094244-06 | SU9516 |

Figure 2A:
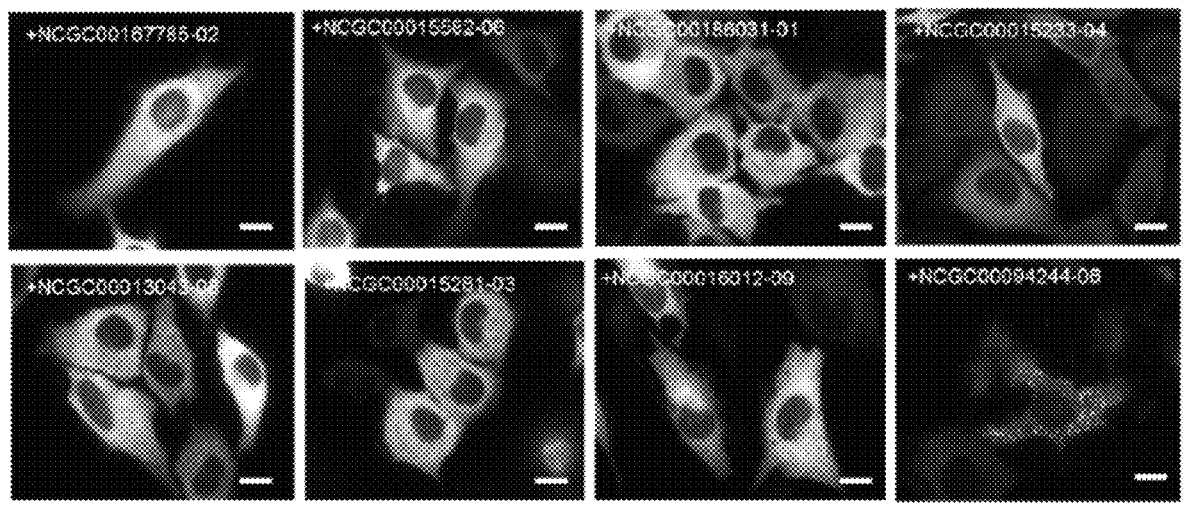
FIG. 2A are images of HeLa-T-PFK1G cells were treated with the 8 hit compounds at 57.5 μM for 5 hours and assessed for their impact on PFK1-mEGFP clustering. The representative images were selected from at least three independent experiments.
Figure 2B:
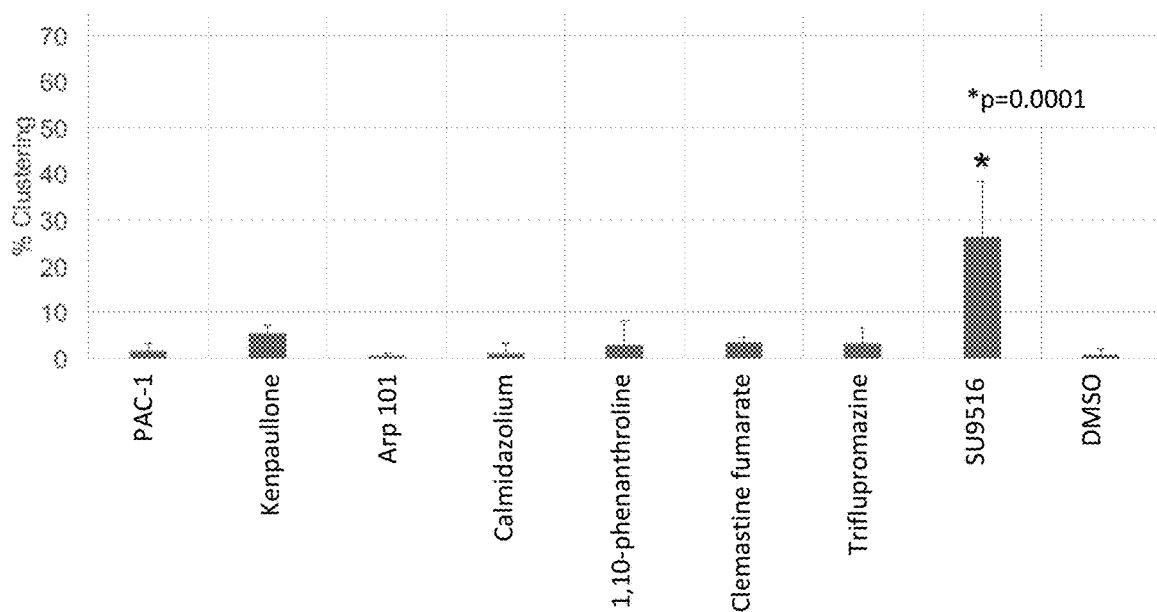
FIG. 2B illustrates the results of the quantitation of the average percentage of cells showing PFK1-mEGFP clustering after treatment with 57.5 μM for 5 hours. Error bars represent the standard deviation of at least three independent trials, statistical significance determined using student's two-tailed t test. Scale bar, 10 μm.
Figure 2C:
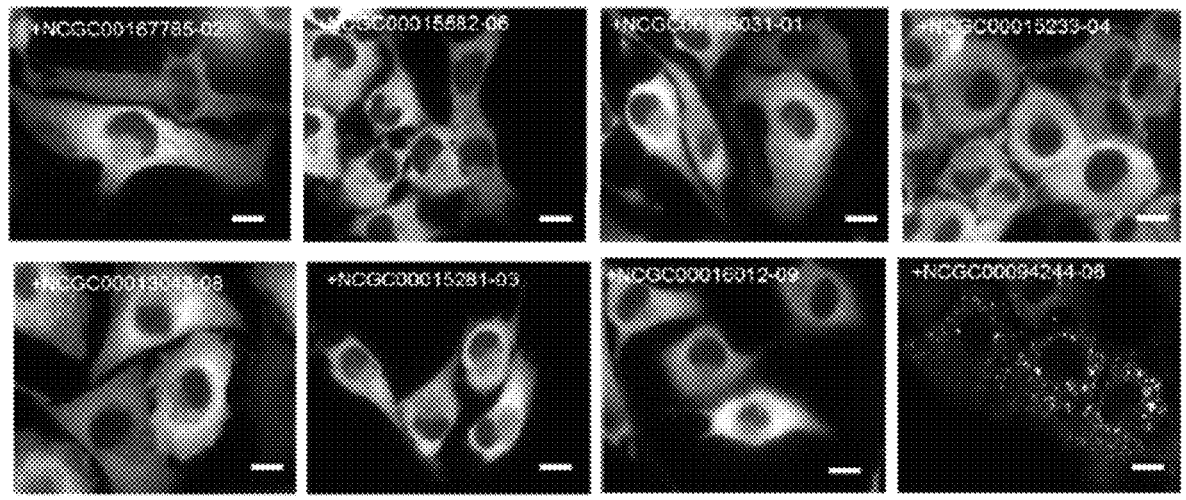
FIG. 2C are images of HeLa-T-PFK1G cells were treated with the 8 hit compounds at 10 μM for 25 hours and assessed for their impact on PFK1-mEGFP clustering. The representative images were selected from at least three independent experiments.
Figure 2D:
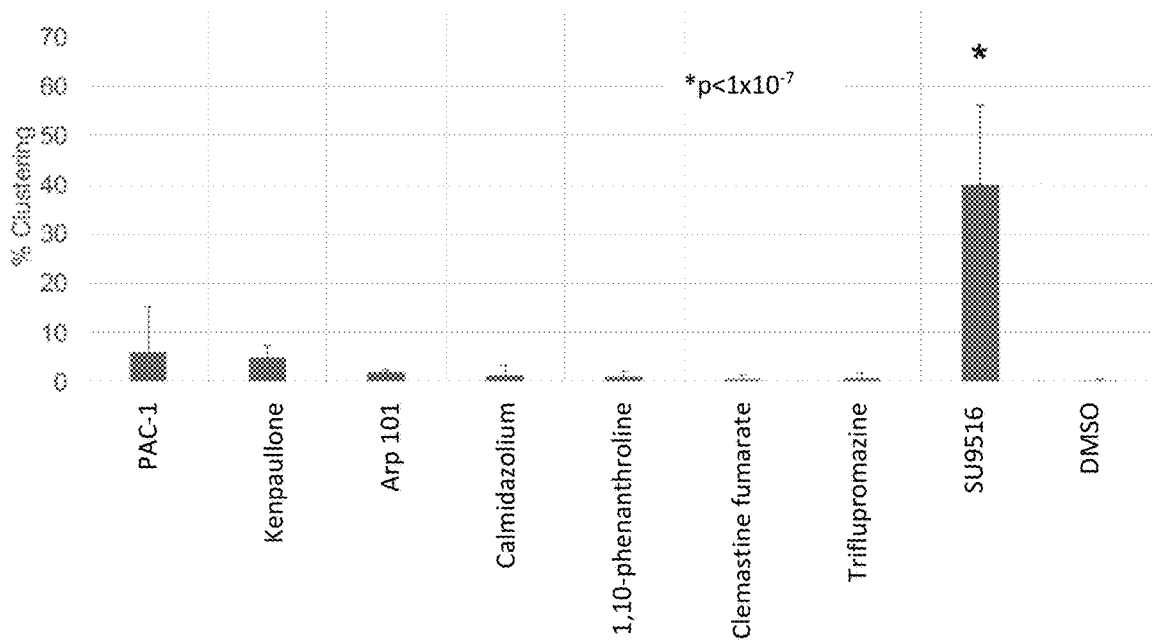
FIG. 2D illustrates the results of the quantitation of the average percentage of cells showing PFK1-mEGFP clustering after treatment with 10 μM for 25 hours. Error bars represent the standard deviation of at least three independent trials, statistical significance determined using student's two-tailed t test. Scale bar, 10 μm.
Figure 3:
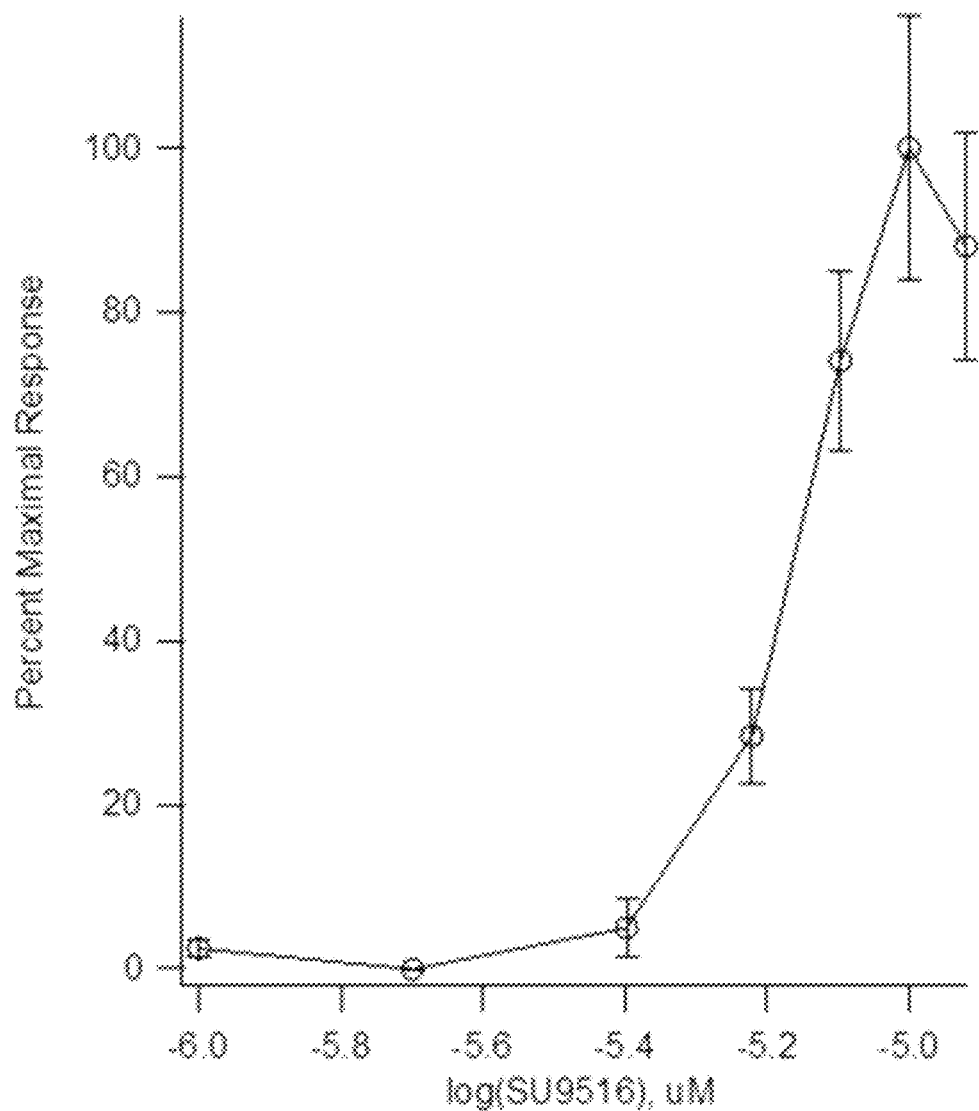
FIG. 3 illustrates the results of the EC50 measurement of SU9516. HeLa-T-PFK1G cells were treated with SU9516 in titration for 25 hours and the number of cells showing the clusters of PFK1-mEGFP was assessed. Error bars represent the standard deviation of at least three independent trials.

Next, the 8 compounds were assessed for their ability to induce PFK1-mEGFP clustering under high-resolution fluorescence microscopy. HeLa-T-PFK1G cells were treated with 57.5 µM for 5 hours (FIGS. 2A and 2B) and 10 µM for 25 hours (FIGS. 2C and 2D). It was discovered that only SU9516 (NCGC00094244-6; 3-[1-(3H-Imidazol-4-yl)-meth-(Z)-ylidene]-5-methoxy-1,3-dihydro-indol-2-one) was capable of inducing PFK1-mEGFP clusters in HeLa-T-PFK1G cells. Quantitatively, SU9516 induced medium- and large-sized PFK1-mEGFP clustering in 26.6±12% of the cells at 57.5 µM for 5 hours, and in 40.0±16% of cells at 10 µM for 25 hours (see, e.g., FIGS. 2B and 2D, respectively). Since approximately 40% displayed medium- and large-sized PFK1-mEGFP clusters in transiently transfected HeLa cells (FIG. 1A), the clustering efficacy induced by SU9516 (i.e., 40.0±16%) in the stably transfected HeLa cells (i.e., HeLa-T-PFK1G) may be a maximum response that a small molecule could induce in HeLa cells. The EC50 of SU9516 with respect to PFK1-mEGFP clustering was determined in HeLa-T-PFK1G cells to be 6.8 µM (see, FIG. 3).

Figure 4:
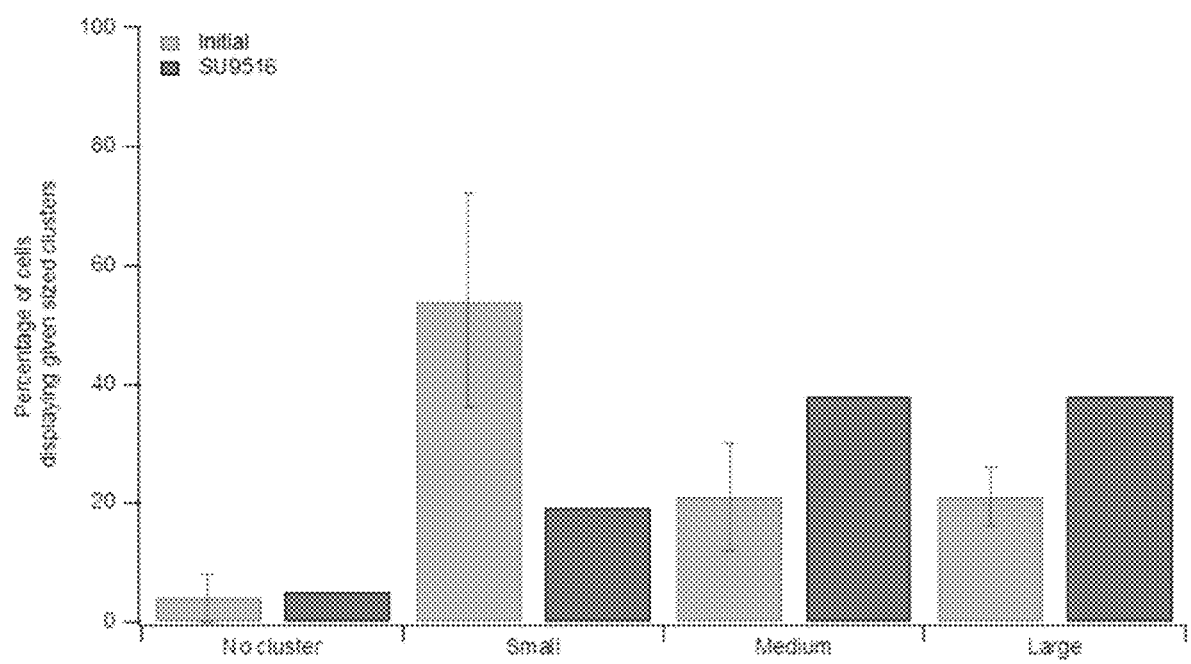
FIG. 4 illustrates the effect of SU9516 on transiently expressed PFK1-mEGFP in HeLa cells. Following treatment, the percent of cell population containing no clusters, small, medium, or large sized clusters were assessed. Error bars represent the standard deviation of three individual trials, otherwise the data represents the average of at least two individual trials. Statistical significance determined using student's two-tailed t test.

As a control, PFK1-mEGFP was transiently transfected into wild-type HeLa cells and treated with SU9516. After 5 hours of treatment with 57.5 µM of SU9516, the promotion of medium- and large-sized clusters from small-sized clusters at single-cell levels were monitored (FIG. 4). The results shown in FIG. 4 further confirms that SU9516 is capable of promoting PFK1-mEGFP clusters in HeLa cells.

Figure 5A:
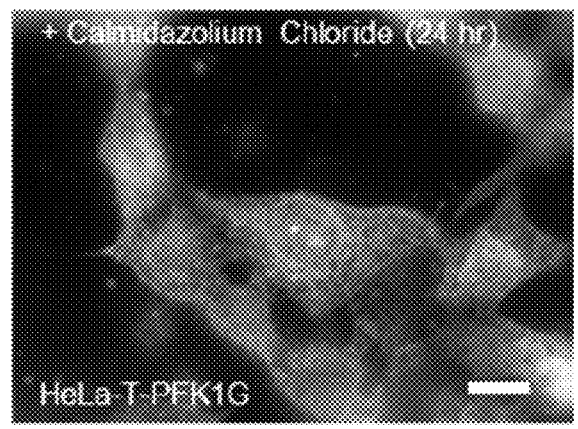
FIG. 5A is an image of a vacuole-type artifact observed following treatment of HeLa-T-PFK1G cells with calmidazolium chloride (10 μM, 24 hr) and cell morphology was observed. Image representative of at least three independent trials.
Figure 5B:
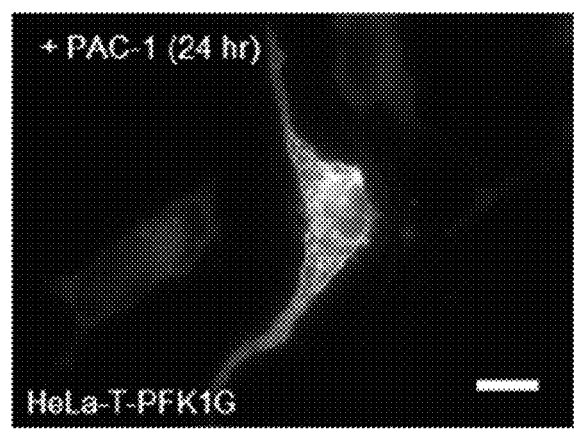
FIG. 5B is an image of a vacuole-type artifact observed following treatment of HeLa-T-PFK1G cells with PAC-1 (10 μM, 24 hr) and cell morphology was observed. Image representative of at least three independent trials.
Figure 5C:
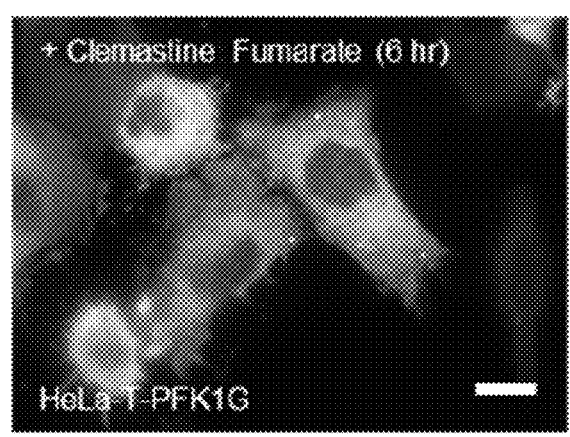
FIG. 5C is an image of protein localization and cell death observed following treatment of HeLa-T-PFK1G cells with clemastine fumarate (57.5 μM, 6 hr) and cell morphology was observed. Image representative of at least three independent trials.

It is noted that the other seven compounds disclosed in Table 1 did not induce PFK1-mEGFP clustering at both conditions. This is anticipated because the qHTS image analysis relies on 20× objective lens (0.45 N.A.) while high-resolution fluorescence microscopy is performed with 60× objective lens (1.45 N.A.). Using high-resolution fluorescence microscopy permits the user to distinguish bonafide PFK1-mEGFP clusters from non-specific subcellular redistributions of PFK1-mEGFP that were caused by small molecule treatment and/or cytotoxicity. For example, some small molecules induced apparent vacuoles in cells or exhibited cytotoxicity (see, FIGS. 5A-5C). Since a cluster in our qHTS image analysis is defined as an area of significantly higher fluorescence intensity over the background, non-specific subcellular redistributions of PFK1-mEGFP could be falsely classified as PFK1-mEGFP clusters. Collectively, SU9516 was the only compound from the LOPAC library (0.078% of library) that effectively induced the clusters of PFK1-mEGFP in HeLa-T-PFK1G cells.

Effect of SU9516 on the Cell Cycle Progression in HeLa Cells

Figure 6B:
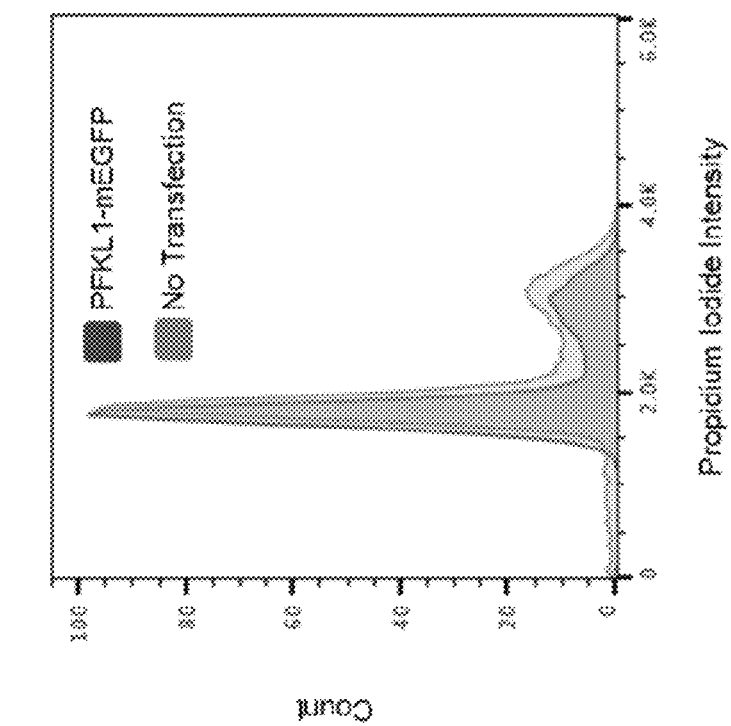
FIG. 6B is a representative histogram of the cell cycle in Hs578T cells both with and without PFK1-mEGFP expression. Histogram selected from at least three individual trials.
Figure 6A:
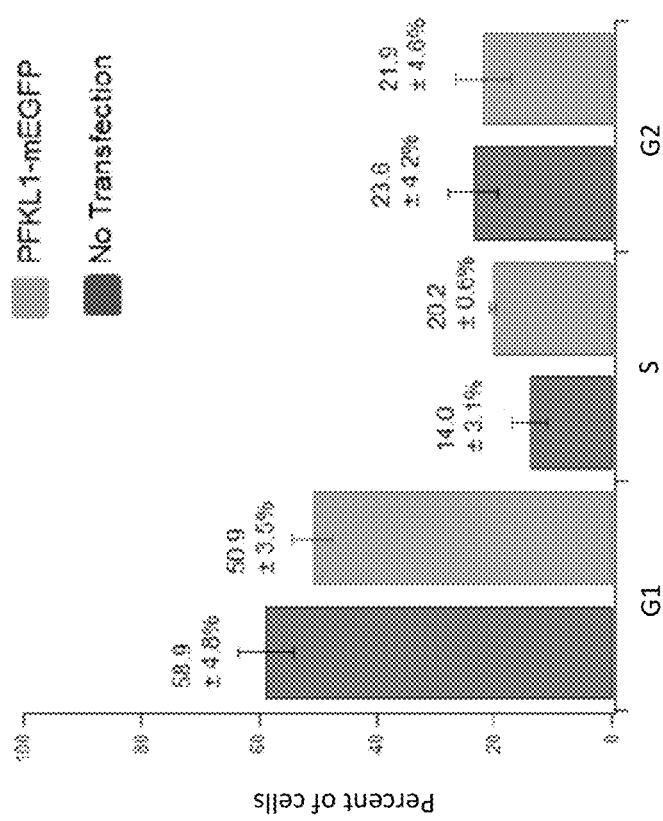
FIG. 6A illustrates the distribution of cells in the G1, S, and G2 phase of the cell cycle of Hs578T breast cancer cells transfected with PFK1-mEGFP versus Hs578T cells which were not transfected. Cell cycle was determined using propidium iodide staining by flow cytometry. Error bars represent the standard deviation of at least three individual trials. Results of an f-test showed no significant differences between the two cell populations in the G1 and G2 phases of the cell cycle (0.6 vs 0.8, respectively). Cells in the S phase, however, demonstrated a significant difference in population distribution (0.03).
Figure 7A:
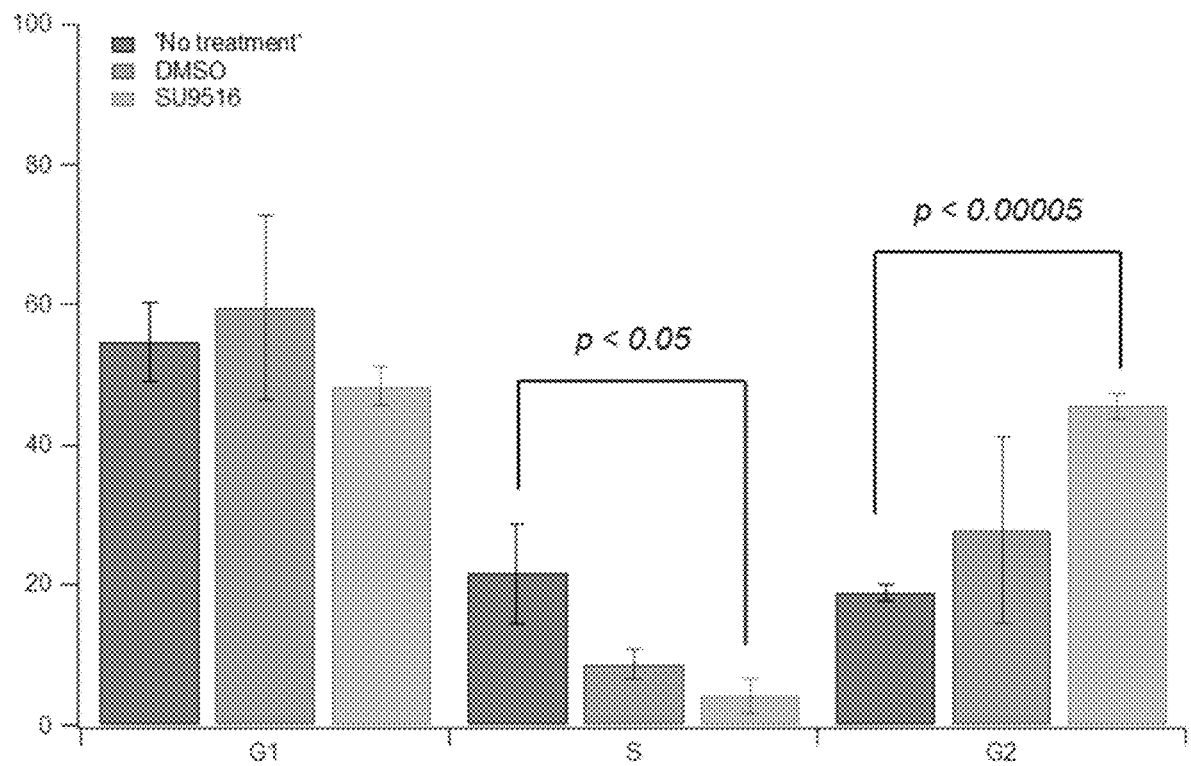
FIG. 7A illustrates the effect of SU9516 on the cell cycle progression of HeLa-T-PFK1G cells. Cells received no small molecules or were treated with DMSO or 10 uM SU9516 and incubated for 24 hours. Then, cells were assessed for cell cycle progression by propidium iodide staining. The changes of the average percentage of cells in each cell cycle following incubation with an indicated compound are shown. Error bars represent the standard deviations of at least three trials and statistical significance was determined using student's two-tailed t test.
Figure 7B:
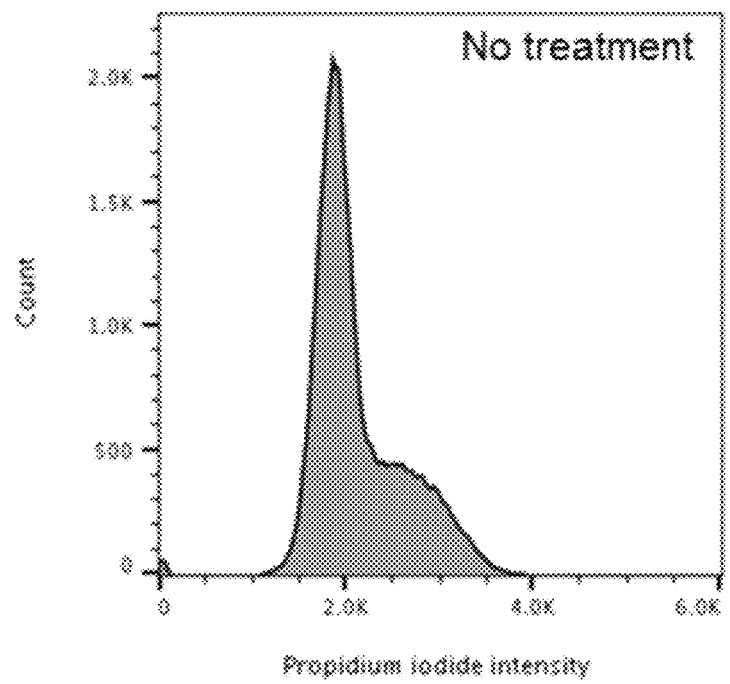
FIG. 7B is a representative histogram of cell cycle progression of HeLa-T-PFK1G cells receiving no treatment. Histograms were selected from at least three independent experiments.
Figure 7C:
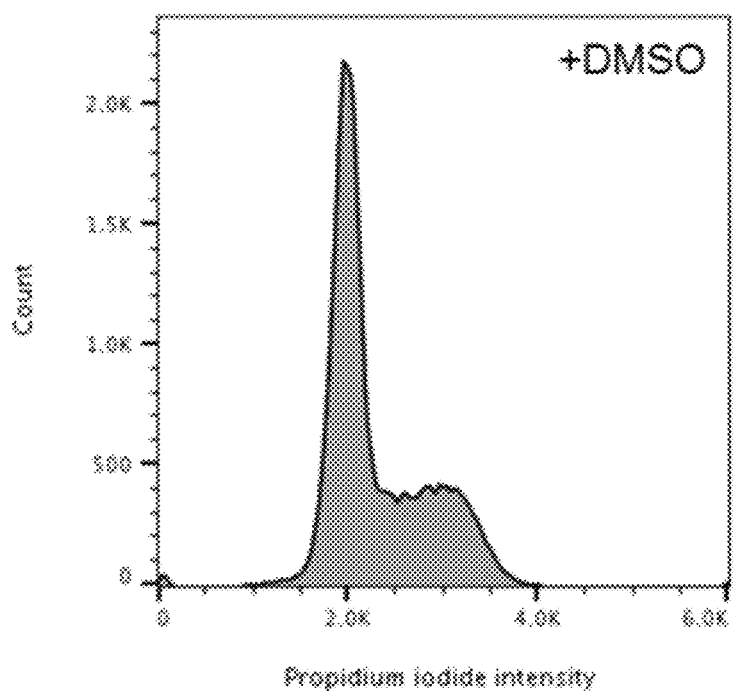
FIG. 7C is a representative histogram of cell cycle progression of HeLa-T-PFK1G cells receiving DMSO for 24 hours. Histograms were selected from at least three independent experiments.
Figure 7D:
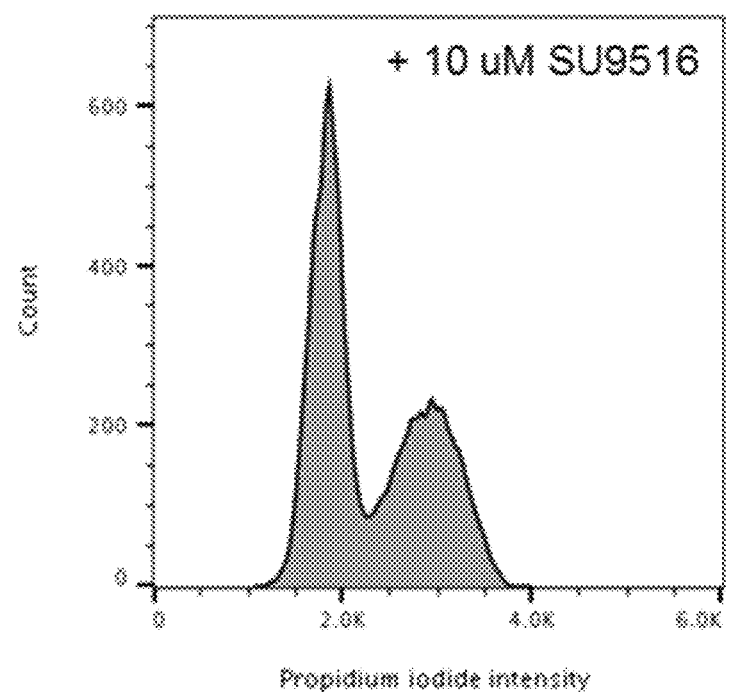
FIG. 7D is a representative histogram of cell cycle progression of HeLa-T-PFK1G cells receiving 10 uM SU9516 for 24 hours. Histograms were selected from at least three independent experiments.

SU9516 was initially developed to inhibit cyclin dependent kinase 2 (CDK2), thus impacting the cell cycle (Lane et al., 2001; Moshinsky et al., 2003; Yu et al., 2002). Experiments were performed to determine if cell cycle progression might play a role in PFK1-mEGFP clustering. As a control, flow cytometry was carried out to confirm that the ectopic expression of PFK1-mEGFP in Hs578T cells did not change the distribution of cell population displaying various phases of the cell cycle (FIGS. 6A-6B). Note that PFK1-mEGFP clusters have been previously characterized in both HeLa and Hs578T cells (Kohnhorst et al., 2017).

Flow cytometry was then performed to determine the effect of 10 µM SU9516 on the cell cycle of HeLa cells after 24 hours treatment. The population of cells in the S phase decreased from 21.5%±7.2% to 4.2%±2.4% in the presence of SU9516, while the population of cells in the G2 phase was significantly increased from 18.9%±1.2% to 45.6%±1.9% with SU9516. However, no significant change was observed in the population of the cells showing the G1 phase (i.e. 54.7%±5.7% vs. 48.4%±2.7%) (FIGS. 7A-7D). Our observation is indeed consistent with previous studies with SU9516 in colon cancers (Lane et al., 2001). Collectively, the promotion of PFK1-mEGFP clustering by SU9516 appears to associate with the changes of cell populations showing different phases of the cell cycle.

Cell-Based qHTS with the LOKI Library

Although SU9516 has an established molecular target, it is an ATP-competitive inhibitor of CDK2 (Lane et al., 2001), and thus its off-targets have been indeed recognized (Anastassiadis et al., 2011). To determine off-target effects of SU9516 on PFK1-mEGFP, a PFK1 clustering assay was performed with the "LOKI" library of 2958 kinase inhibitors. The LOKI library consists of three smaller libraries; including i) the published kinase inhibitor set, ii) Roche kinase inhibitor library, and the mechanism interrogation plates. Importantly, it includes a number of inhibitors that primarily target various isoforms of CDK as well as known off-targets of SU9516.

In this work, HeLa-T-PFK1G cells were treated with the LOKI library and subsequently fixed and analyzed (Table 2). Based on the efficacy of compounds in our assay (Inglese et al., 2007), 25 compounds induced PFK1-mEGFP clustering and exhibited a curve class of 1.1, and 41 compounds exhibited a curve class of 1.2. In addition, 167 compounds demonstrated a curve of 2, while 78 compounds exhibited a curve class of 3, with the rest of the compounds having inconclusive or no effect (curve classes of 4 and 5). However, it was also noticed that many or if not all of their apparent effects to induce PFK1-mEGFP clustering seem to correlate with high cytotoxicity. Compounds that caused apparent cytotoxicity and also that induced experimental artifacts due to the precipitation of compounds were eliminated. Accordingly, positive hit compounds were further narrowed down to a total 24 compounds; 7 compounds of a curve class 1, and 17 compounds of a curve class 2 (Table 3). Overall, the second qHTS was able to identify several kinase inhibitors that induce clustering of PFK1-mEGFP with minimum cytotoxicity.

TABLE 2

Curve class distribution of small molecules in the LOKI screen

| Curve class | 1.1/−1.1 | 1.2/−1.2 | 2.1/−2.1 | 2.2/−2.2 | 3/−3 | 4 | 5 |
|---|---|---|---|---|---|---|---|
| PFK1-mEGFP clustering | 25/1 | 41/41 | 61/0 | 106/3 | 78/0 | 2600 | 2 |

TABLE 3

Small molecules from the LOKI induced PFK1-mEGFP clustering.

| NCGC ID | Curve Class | Primary Target | Reference |
|---|---|---|---|
| NCGC00346698-01 | 1.1/1.2 | mTORC1/2 inhibitor | Pike et al Bioorg Med Chem Lett 23 1212-6 (2013) |

TABLE 3-continued

Small molecules from the LOKI induced PFK1-mEGFP clustering.

| NCGC ID | Curve Class | Primary Target | Reference |
|---|---|---|---|
| NCGC00094087-06 | 1.1/1.2 | inosine 5'-Monophosphate Dehydrogenase (IMPDH) inhibitors | Koyama et al Biochem Pharmacol 32 3547-53 (1983) |
| NCGC00018248-08 | 1.1/1.2 | Cyclooxygenase-1/2 inhibitor | Noble et al Drugs 51 424-30 (1996) |
| NCGC00159346-05 | 1.1/1.2 | Fungal Squalene Monooxygenase inhibitor | Ryder Clin Exp Dermatol 14 98-100 (1989) |
| NCGC00263213-01 | 1.1/1.2 | IKK-2 (IKK-beta) Inhibitor | Sommers et al J Pharmacol Exp Ther 330 377-88 (2009) |
| NCGC00346518-01 | 1.1/1.2 | Carbapenem Antibiotic | Pryka Ann Pharmacother 28 1045-54 (1994) |
| NCGC00344512-01 | 1.1/1.2 | Opioid receptor antagonist | Schmidhammer et al J Med Chem 32 418-21 (1989) |
| NCGC00346747-02 | 2.1 | NFkappaB-inducing kinase inhibitor | USA Patent US2011086834 |
| NCGC00015420-09 | 2.1/2.2 | Casein Kinase II (CK2) inhibitor | Srinivas et al Med Res Rev 27 591-608 (2007) |
| NCGC00263125-01 | 2.1/2.2 | mTORC1/2 inhibitor | Weinberg Anticancer Drugs 27 475-87 (2016) |
| NCGC00346681-01 | 2.1/2.2 | PI3K Inhibitor | Chang et al Clin Cancer Res 15 7116-26 (2011) |
| NCGC00165811-03 | 2.1/2.2 | inhibitor of nuclear factor kappa b kinase subunit beta (IKK-2) Inhibitor | Onai et al Cardiovasc Res 83 51-9 (2004) |
| NCGC00347280-01 | 2.1/2.2 | IKK-2 (IKK-beta) inhibitor | Murata et al Bioorg Med Chem Lett 14 4019-22 (2004) |
| NCGC00166111-04 | 2.1/2.2 | Estrogen Receptor (ER) Agonist (nuclear) | Clark et al J Anim Sci 49 46-65 (1979) |
| NCGC00181306-03 | 2.1/2.2 | Tubulin depolymerization inhibitor | Plenta Semin Oncol 28 3-7 (2001) |
| NCGC00167513-03 | 2.1/2.2 | EGFR (HER1; erbB1) Inhibitor | Hennequin et al J Med Chem 45 1300-12 (2002) |
| NCGC00241982-03 | 2.1/2.2 | ROCK 1, ROCK 2 inhibitor | Stavenger et al J Med Chem 50 2-5 (2007) |
| NCGC00346893-01 | 2.1/2.2 | MAPKAP-K1 (RSK; p90Rsk) Inhibitor | Smith et al Cancer Res 65 1027-34 (2005) |
| NCGC00346959-01 | 2.1/2.2 | Lck Kinase inhibitors | Martin et al J Med Chem 49 4981-91 (2006) |
| NCGC00348107-01 | 2.1/2.2 | CSF1R (c-FMS) Inhibitor | U.S. Pat. 7,705,042 |
| NCGC00346542-01 | 2.1/2.2 | Aurora kinase inhibitor | Hauf et al Journal of Cell Biology 161 281-94 (2003) |
| NCGC00346652-01 | 2.1/2.2 | Aurora kinase inhibitor | Jani et al Mol Cancer Ther 9 863-94 (2010) |
| NCGC00346553-01 | 2.1/2.2 | CDK7 | Ali et al Cancer Res 69 6208-15(2009) |
| NCGC00263129-01 | 2.1/2.2 | CDK4, 6 | Fry et al Mol Cancer Ther 3 1427-38 (2004) |

Figure 8A:
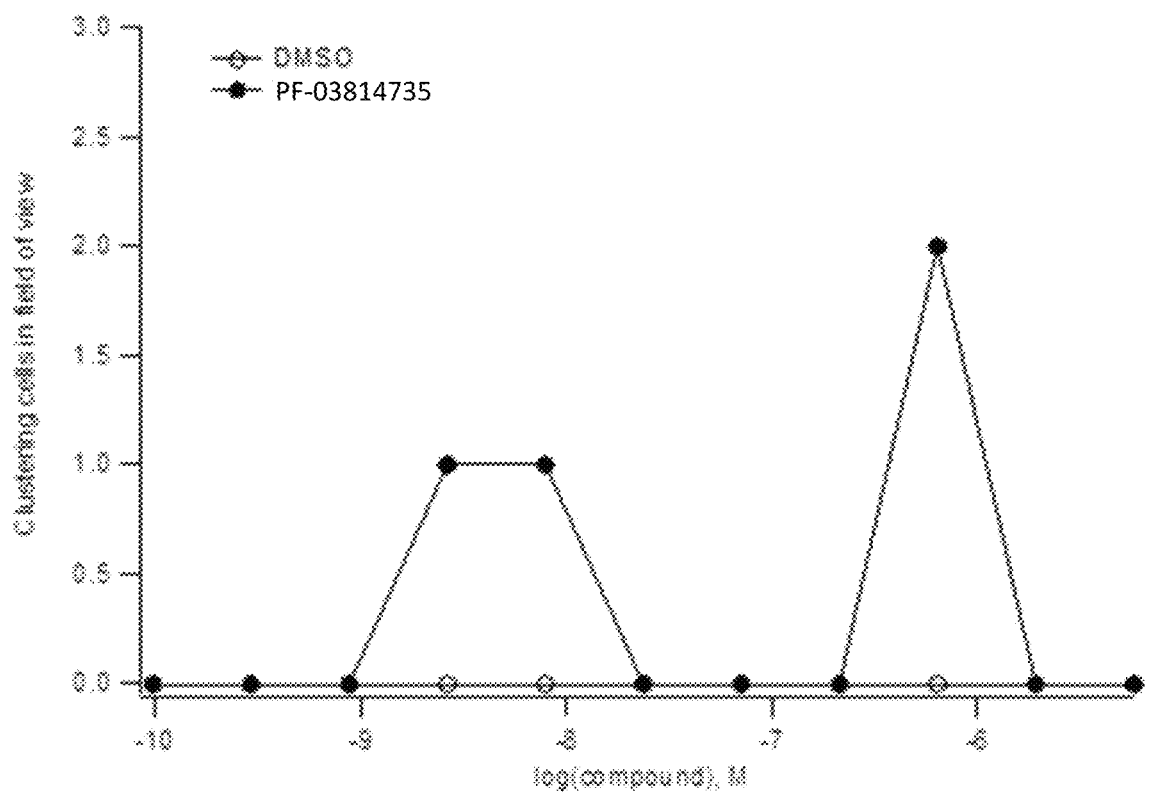
FIG. 8A illustrates the results of the effect of PF-03814735 on PFK1-mEGFP clustering in HeLa-T-PFK1G cells.
Figure 8B:
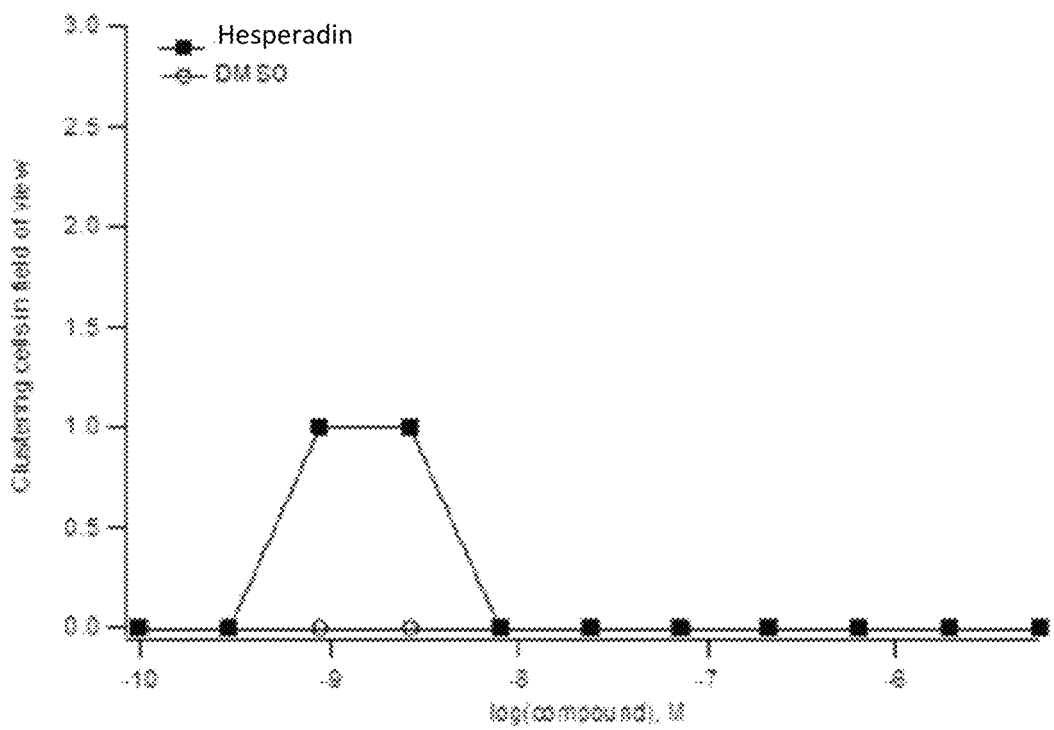
FIG. 8B illustrates the results of the effect of Hesperadin on PFK1-mEGFP clustering in HeLa-T-PFK1G cells.
Figure 8C:
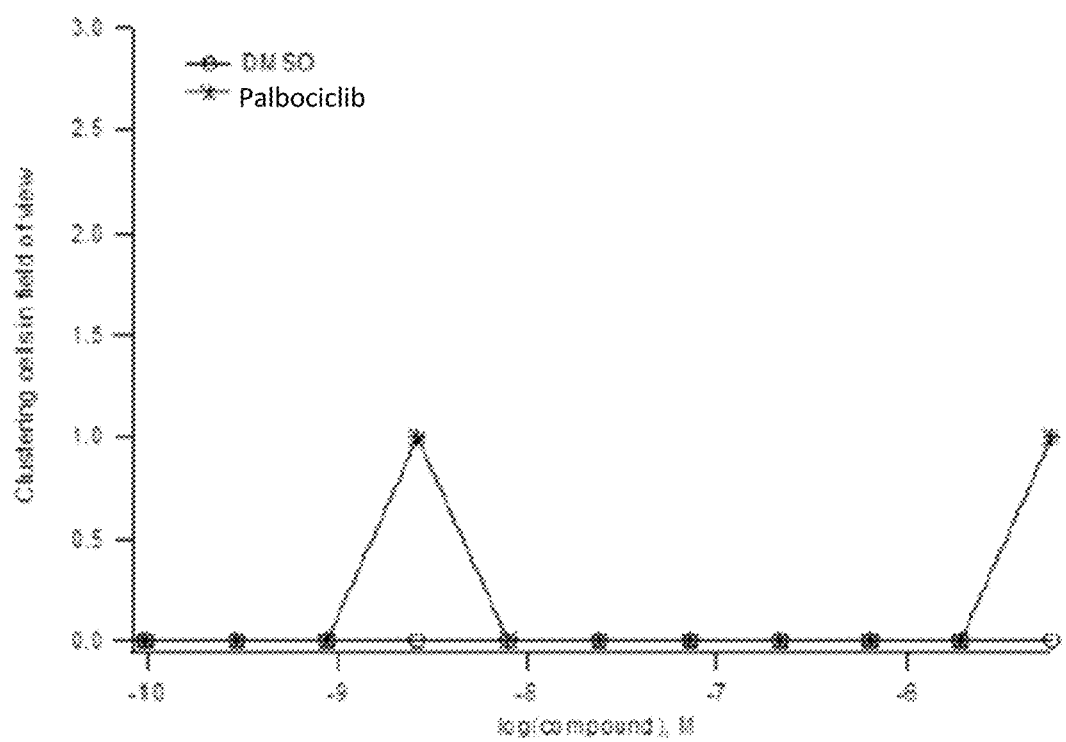
FIG. 8C illustrates the results of the effect of Palbociclib on PFK1-mEGFP clustering in HeLa-T-PFK1G cells.

Of the 16 hit compounds from the LOKI library, 5 were found to have targets which are known off-targets of SU9516 (Ali et al., 2009; Anastassiadis et al., 2011; Bain et al., 2007; Hauf et al., 2003; Jani et al., 2010; Nomanbhoy et al., 2016a). Such off-targets include Aurora kinases, CDK4/6, CDK7, and ribosomal protein S6 kinase (Table 4). Interestingly, the majority of these proteins are primarily involved in the cell cycle progression, indicating the association of PFK1 clustering with the cell cycle progression (Ali et al., 2009; Fry et al., 2004; Hauf et al., 2003; Jani et al., 2010). However, when the assay was repeated, the inhibitors of CDK7 (NCGC00346553-01; BS-181) and ribosomal S6 kinase (NCGC00346893-01; SL-0101-1) did not promote PFK1-mEGFP clustering while the other three compounds, PF-03814735 (NCGC00346652-01, Aurora kinase inhibitor), Hesperadin (NCGC00346542-1, Aurora B kinase inhibitor), and Palbociclib (NCGC00263129-24, CDK 4/6inhibitor) induced PFK1-mEGFP clustering (FIGS. 8A-8C). Since Palbociclib is a CDK 4/6inhibitor, it is not possible to entirely discount the effect of CDKs on PFK1-mEGFP clustering. On the other hand, it is also important to emphasize here that despite the inclusion of at least 7 well-established CDK inhibitors in the LOKI screen, each of which target several CDK isoforms (including CDK1, CDK2, CDK4, CDK7, and/or CDK9) (Table 5), these compounds were not identified in the final 16 positive hits (Table 3), indicating that the cellular effect of CDK2 inhibition by SU9516 might be suppressed by off-target inhibitions of other kinases. Collectively, PFK1 clustering by SU9516 may represent collective effects from both the CDK2 inhibition and the SU9516-associated off-target inhibitions.

TABLE 4

Small molecules from the LOKI screen which inhibit the off-targets of SU9516.

| NCGC ID | Curve Class | Compound Name |
|---|---|---|
| NCGC00346542-01 | 2.1 | Hesperadin |
| NCGC00346652-01 | 2.1 | PF-03814735 |
| NCGC00346553-01 | 2.1 | BS-181 |
| NCGC00263129-01 | 2.1 | Palbociclib |
| NCGC00346893-01 | 2.1 | SL-0101-1 |

TABLE 5

CDK Inhibitors screened but did not induce PFK1-mEGFP clustering.

| NCGC ID | Primary Target | Off-target CDK | Curve class | Reference |
|---|---|---|---|---|
| NCGC00345632-01 | CDK1, CDK2, CDK4 | CDK7 | −2.1 | De-Pinto et al Mol Cancer Ther 5 2644-56 (2006) |

TABLE 5-continued

CDK Inhibitors screened but did not induce PFK1-mEGFP clustering.

| NCGC ID | Primary Target | Off-target CDK | Curve class | Reference |
|---|---|---|---|---|
| NCGC00263091-01 | CDK2 | CDK1, CDK4, CDK5 | −1.3 | Santo et al Oncogene 29 2325-38 (2010) |
| NCGC00094374-01 | CDK2, CDK7, CDK9 | CDK8 | −2.1, 3 | Meijer et al Eur J Biochem 243 527-36 (1997) |
| NCGC00263187-01 | CDK2 | CDK1, CDK4, CDK7, CDK9 | −2.4 | Misra J Med Chem 47 1719-28 (2004) |
| NCGC00346893-01 | CDK1, CDK2 | CDK4 | 4 | Misra Bioorg Med Chem Lett 13 2405-8 (2003) |
| NCGC00250401-01 | CDK9 | CDK1, CDK2, CDK4, CDK4 | 4 | Carlson et al Cancer Red 56 2973-6 (1996) |
| NCGC00015763-01 | CDK1, CDK2 |  | 4 | Giab et al FEBS Lett 353 207-11 (1994) |

Discussion

Spatial assemblies of metabolic enzymes involved in human glucose metabolism have been identified in cancer cells (Jin et al., 2017; Kohnhorst et al., 2017; Webb et al., 2017), but their assembly mechanisms remain to be elucidated. In this study, qHTS technology was used to unveil the assembly mechanism of the enzyme clusters in HeLa cells.

Employing two small molecule libraries (i.e., LOPAC and LOKI), cell cycle-modulating small molecules that promote the formation of PFK1-mEGFP clusters in HeLa cells were identified. Given that PFK1-mEGFP is a representative for the multienzyme metabolic complex involved in human glucose metabolism, namely the glucosome (Kohnhorst et al., 2017; Jeon et al., 2018), the results strongly suggest that the cell cycle regulators are tightly associated with the formation of glucosome clusters in human cancer cells.

At the same time, the present study demonstrates that the reversibility of PFK1-mEGFP in live cells can be employed as an intracellular reporter for qHTS technology to dissect the assembly mechanism of enzyme compartments in live cells. In recent years, many metabolic enzymes have been found to be reversibly localized within mammalian cells into clusters, rings, rods, and/or filaments (Schmitt and An, 2017), however, the underlying mechanisms that regulate the formation of such enzyme compartments are largely unknown (Schmitt and An, 2017). It was demonstrated that qHTS technology was advantageous to determine and validate the cell cycle-dependent formation of PFK1 clusters in HeLa cells. In addition, primary protein regulators were identified that assist in the determination of the mechanisms of glucosome clustering in HeLa cells. However, it is also important to note here that vigorous follow-up screening and validation experiments were essential to eliminate false positives from the initial hits because of the difference between the optical settings of the high-content imager and the high-resolution fluorescence microscope. Therefore, beyond the well-defined contributions of qHTS assays to novel drug discovery, the study alternatively emphasizes the importance of qHTS as a useful technology to understand the assembly mechanism of enzyme compartments in live cells.

It was also discovered that SU9516 is the only compound from the LOPAC library promoting the PFK1-mEGFP clusters in HeLa cells. SU9516 was initially developed as an ATP-competitive, selective CDK2 inhibitor, with a moderate preference to the CDK2/cyclin A complex over the CDK2/cyclin E complex (Lane et al., 2001; Moshinsky et al., 2003). In cancer cells, SU9516 was found to decrease the population of cells in the S phase of the cell cycle, but promote the population of cells in the G2/M phase, and eventually trigger apoptosis after >48 hr incubations (Lane et al., 2001). SU9516 treatment also prevented the epithelial-mesenchymal transition in tumor metastasis (Arai et al., 2016). More recently, SU9516 was discovered as a novel alpha-7 integrin-enhancing compound in muscle and showed its beneficial effect on a mouse model of Duchenne muscular dystrophy (Sarathy et al., 2017). In this work, the regulatory mechanism of SU9516 at molecular levels was unveiled, wherein the spatial assembly of enzyme complexes involved in glucose metabolism, the glucosome, is significantly stimulated in a cell cycle-dependent manner in cancer cells.

In addition, based on the LOPAC and LOKI library screening, it is proposed that SU9516 regulates PFK1-mEGFP clustering through not only the inhibition of CDK2 but also its off-target effects. Based on the applied concentration of SU9516 (10 uM), its off-target effects cannot be ruled out. These off-targets, including Aurora kinases and CDK4/6 (Anastassiadis et al., 2011), are all implicated in the cell cycle regulation (Anjum and Blenis, 2008; Asghar et al., 2015; Carmena and Earnshaw, 2003; Endicott and Noble, 2013; Hauf et al., 2003; Jani et al., 2010; Nomanbhoy et al., 2016b; Smith et al., 2005; Wang et al., 2016). The data indicates that CDK2, Aurora kinases, and CDK4/6 may contribute to some extent to the clustering of PFK1. Although in-depth investigation studying the detailed mechanisms of their actions on PFK1 clustering is necessary, it is apparent that the formation of PFK1-mEGFP assemblies (i.e. glucosome formation) is tightly associated with the cell cycle progression, during which these protein kinases may play essential roles.

Interestingly, CDK2 and Aurora kinases have been previously shown to influence glycolysis as well. In HeLa cells, CDK2 was found to decrease the activity of triosephosphate isomerase by direct phosphorylation (Lee et al., 2010). Additionally, knockdown of hexokinase II has been demonstrated to stall cells in the G1 phase through the enhanced phosphorylation on CDK2, resulting in the inhibition of CDK2 in fibroblasts. (Hu et al., 2014). In leukemia cells, glycolysis was upregulated in the presence of Aurora kinase inhibitors as measured by glucose uptake and lactate production (Liu et al., 2013). Aside from their roles in the cell cycle, CDK2 and Aurora kinases are clearly implicated in the regulation of glycolysis.

It is also important to discuss here the relationship between the cell cycle and glucose metabolism. Glycolysis and directly associated metabolic pathways provide building blocks and energy for various cellular processes, including the cell cycle (Kalucka et al., 2015; Roy et al., 2017; Salazar-Roa and Malumbres, 2017). Glycolysis is regulated on both transcriptional and post-translational levels throughout the cell cycle (Salazar-Roa and Malumbres, 2017). It has been also well established that the regulation of PFK1 by various allosteric activators and inhibitors is essential for controlling glycolysis in a cell cycle-dependent manner (Bensaad et al., 2006; Doménech et al., 2015; Mor et al., 2011). Cells which have committed to undergo mitosis upregulate the key glycolytic regulatory enzyme PFKFB3

(Chesney, 2006; Yalcin et al., 2014) in the G1 phase, resulting in the upregulation of glycolysis. Increased glycolysis is also sustained until PFKFB3 is targeted for degradation in the late S phase, which ties with the upregulation of the pentose phosphate pathway in the S phase (Kaplon et al., 2015). Furthermore, the activities of several glycolytic enzymes, namely pyruvate kinase muscle type 2 and hexokinase, are regulated by the cell cycle-associated proteins (e.g. cyclin D, CDK4/6, and ligase anaphase-promoting complex or cyclosome) (Kaplon et al., 2015; Salazar-Roa and Malumbres, 2017). Although the metabolic consequences of PFK1 clustering are not fully understood yet (Kohnhorst et al., 2017), it stands to reason that the alteration of PFK1 compartmentalization throughout the cell cycle plays a key role in managing glucose flux.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art, based on the disclosure herein. The invention therefore is to be broadly construed, as encompassing all such variations, modifications and alternative embodiments within the spirit and scope of the claims hereafter set forth.

REFERENCES

Ali, S., Heathcote, D. A., Kroll, S. H. B., Jogalekar, A. S., Scheiper, B., Patel, H., Brackow, J., Siwicka, A., Fuchter, M. J., Periyasamy, M., et al. (2009). The development of a selective cyclin-dependent kinase inhibitor that shows antitumor activity. *Cancer Research*, 69, 6208-6215.

An, S., Kumar, R., Sheets, E. D., and Benkovic, S. J. (2008). Reversible compartmentalization of de novo purine biosynthetic complexes in living cells. *Science*, 320, 103-106.

Anastassiadis, T., Deacon, S. W., Devarajan, K., Ma, H., and Peterson, J. R. (2011). Comprehensive assay of kinase catalytic activity reveals features of kinase inhibitor selectivity. *Nature Biotechnology*, 29, 1039-1045.

Anjum, R., and Blenis, J. (2008). The RSK family of kinases: emerging roles in cellular signalling. *Nat Rev Mol Cell Biol*, 9, 747-758.

Arai, K., Eguchi, T., Rahman, M. M., Sakamoto, R., Masuda, N., Nakatsura, T., Calderwood, S. K., Kozaki, K.-I., and Itoh, M. (2016). A Novel High-Throughput 3D Screening System for EMT Inhibitors: A Pilot Screening Discovered the EMT Inhibitory Activity of CDK2 Inhibitor SU9516. *PLoS ONE*, 11, e0162394-18.

Asghar, U., Witkiewicz, A. K., Turner, N.C., and Knudsen, E. S. (2015). The history and future of targeting cyclin-dependent kinases in cancer therapy. *Nat Rev Drug Disc*, 14, 130-146.

Bain, J., Plater, L., Elliott, M., Shpiro, N., Hastie, C. J., Mclauchlan, H., Klevernic, I., Arthur, J. S. C., Alessi, D. R., and Cohen, P. (2007). The selectivity of protein kinase inhibitors: a further update. *Biochem. J.*, 408, 297-315.

Bensaad, K., Tsuruta, A., Selak, M. A., Vidal, M. N. C., Nakano, K., Bartrons, R., Gottlieb, E., and Vousden, K. H. (2006). TIGAR, a p53-Inducible Regulator of Glycolysis and Apoptosis. *Cell* 126, 107-120.

Bitterman, J. L., and Chung, J. H. (2014). Metabolic effects of resveratrol: addressing the controversies. *Cell. Mol. Life Sci.*, 72, 1473-1488.

Borisa, A. C., and Bhatt, H. G. (2017). A comprehensive review on Aurora kinase: Small molecule inhibitors and clinical trial studies. *European Journal of Medicinal Chemistry*, 140, 1-19.

Carmena, M., and Earnshaw, W. C. (2003). The cellular geography of aurora kinases. *Nat Rev Mol Cell Biol*, 4, 842-854.

Chesney, J. (2006). 6-phosphofructo-2-kinase/fructose-2,6-bisphosphatase and tumor cell glycolysis. *Curr Opin Clin Nutr Metab Care*, 9, 535-539.

Chu, H., and Low, P. S. (2006). Mapping of glycolytic enzyme-binding sites on human erythrocyte band 3. *Biochem. J.*, 400, 143-151.

Crowley, L. C., Chojnowski, G., and Waterhouse, N. J. (2016). Measuring the DNA Content of Cells in Apoptosis and at Different Cell-Cycle Stages by Propidium Iodide Staining and Flow Cytometry. *Cold Spring Harb Protoc*, 2016, pdb.prot087247.

Deprez, J., Vertommen, D., Alessi, D. R., Hue, L., and Rider, M. H. (1997). Phosphorylation and activation of heart 6-phosphofructo-2-kinase by protein kinase B and other protein kinases of the insulin signaling cascades. *J. Biol. Chem.*, 272, 17269-17275.

Doménech, E., Maestre, C., Esteban-Martinez, L., Partida, D., Pascual, R., Fernandez-Miranda, G., Seco, E., Campos-Olivas, R., Perez, M., Megias, D., et al. (2015). AMPK and PFKFB3 mediate glycolysis and survival in response to mitophagy during mitotic arrest. *Nat Cell Biol*, 17, 1304-1316.

Endicott, J. A., and Noble, M. E. M. (2013). Structural characterization of the cyclin-dependent protein kinase family. *Biochem. Soc. Trans.*, 41, 1008-1016.

Fox, M. H. (1980). A model for the computer analysis of synchronous DNA distributions obtained by flow cytometry. *Cytometry*, 1, 71-77.

Fry, D. W., Harvey, P. J., Keller, P. R., Elliott, W. L., Meade, M., Trachet, E., Albassam, M., Zheng, X., Leopold, W. R., Pryer, N. K., et al. (2004). Specific inhibition of cyclin-dependent kinase 4/6 by PD 0332991 and associated antitumor activity in human tumor xenografts. *Molecular Cancer Therapeutics*, 3, 1427-1438.

Gomez, L. S., Zancan, P., Marcondes, M. C., Ramos-Santos, L., Meyer-Fernandes, J. R., Sola-Penna, M., and Da Silva, D. (2013). Resveratrol decreases breast cancer cell viability and glucose metabolism by inhibiting 6-phosphofructo-1-kinase. *Biochimie*, 95, 1336-1343.

Haney, S. A., LaPan, P., Pan, J., and Zhang, J. (2006). High-content screening moves to the front of the line. *Drug Discovery Today*, 11, 889-894.

Hauf, S., Cole, R. W., LaTerra, S., Zimmer, C., Schnapp, G., Walter, R., Heckel, A., van Meel, J., Rieder, C. L., and Peters, J.-M. (2003). The small molecule Hesperadin reveals a role for Aurora B in correcting kinetochore-microtubule attachment and in maintaining the spindle assembly checkpoint. *The Journal of Cell Biology*, 161, 281-294.

Hu, J.-W., Sun, P., Zhang, D.-X., Xiong, W.-J., and Mi, J. (2014). Hexokinase 2 regulates G1/S checkpoint through CDK2 in cancer-associated fibroblasts. *Cellular Signalling*, 26, 2210-2216.

Hydbring, P., Malumbres, M., and Sicinski, P. (2016). Non-canonical functions of cell cycle cyclins and cyclin-dependent kinases. *Nature Publishing Group*, 17, 280-292.

Inglese, J., Auld, D. S., Jadhav, A., Johnson, R. L., Simeonov, A., Yasgar, A., Zheng, W., and Austin, C. P. (2006). Quantitative high-throughput screening: A titration-based approach that efficiently identifies biological activities in large chemical libraries. *Proc Natl Acad Sci USA*, 103, 11473-11478.

Inglese, J., Johnson, R. L., Simeonov, A., Xia, M., Zheng, W., Austin, C. P., and Auld, D. S. (2007). High-throughput screening assays for the identification of chemical probes. *Nat Chem Biol*, 3, 466-479.

Jani, J. P., Arcari, J., Bernardo, V., Bhattacharya, S. K., Briere, D., Cohen, B. D., Coleman, K., Christensen, J. G., Emerson, E. O., Jakowski, A., et al. (2010). PF-03814735, an Orally Bioavailable Small Molecule Aurora Kinase Inhibitor for Cancer Therapy. *Molecular Cancer Therapeutics*, 9, 883-894.

Jeon, M., Kang, H.-W., An, S. (2018) A Mathematical Model for Enzyme Clustering in Glucose Metabolism. *Scientific Reports*, 8, 2696.

Jin, M., Fuller, G. G., Han, T., Yao, Y., Alessi, A. F., Freeberg, M. A., Roach, N. P., Moresco, J. J., Karnovsky, A., Baba, M., et al. (2017). Glycolytic Enzymes Coalesce in G Bodies under Hypoxic Stress. *Cell Reports*, 20, 895-908.

Johnson, D. G., and Walker, C. L. (1999). Cyclins and cell cycle checkpoints. *Annu. Rev. Pharmacol. Toxicol.*, 39, 295-312.

Kalucka, J., Missiaen, R., Georgiadou, M., Schoors, S., Lange, C., De Bock, K., Dewerchin, M., and Carmeliet, P. (2015). Metabolic control of the cell cycle. *Cell Cycle*, 14, 3379-3388.

Kaplon, J., van Dam, L., and Peeper, D. (2015). Two-way communication between the metabolic and cell cycle machineries: the molecular basis. *Cell Cycle*, 14, 2022-2032.

Kohnhorst, C. L., Kyoung, M., Jeon, M., Schmitt, D. L., Kennedy, E. L., Ramirez, J., Bracey, S. M., Luu, B. T., Russell, S. J., and An, S. (2017). Identification of a multienzyme complex for glucose metabolism in living cells. *J. Biol. Chem.*, 292, 9191-9203.

Korn, K., and Krausz, E. (2007). Cell-based high-content screening of small-molecule libraries. *Current Opinion in Chemical Biology*, 11, 503-510.

Lane, M. E., Yu, B., Rice, A., Lipson, K. E., Liang, C., Sun, L., Tang, C., McMahon, G., Pestell, R. G., and Wadler, S. (2001). A novel cdk2-selective inhibitor, SU9516, induces apoptosis in colon carcinoma cells. *Cancer Research*, 61, 6170-6177.

Lee, W.-H., Choi, J.-S., Byun, M.-R., Koo, K.-T., Shin, S., Lee, S.-K., and Surh, Y.-J. (2010). Functional inactivation of triosephosphate isomerase through phosphorylation during etoposide-induced apoptosis in HeLa cells: Potential role of Cdk2. *Toxicology*, 278, 224-228.

Liu, L. L., Long, Z. J., Wang, L. X., Zheng, F. M., Fang, Z. G., Yan, M., Xu, D. F., Chen, J. J., Wang, S. W., Lin, D. J., et al. (2013). Inhibition of mTOR Pathway Sensitizes Acute Myeloid Leukemia Cells to Aurora Inhibitors by Suppression of Glycolytic Metabolism. *Molecular Cancer Research*, 11, 1326-1336.

Michael, S., Auld, D., Klumpp, C., Jadhav, A., Zheng, W., Thorne, N., Austin, C. P., Inglese, J., and Simeonov, A. (2008). A Robotic Platform for Quantitative High-Throughput Screening. *ASSAY and Drug Development Technologies*, 6, 637-657.

Mor, I., Cheung, E. C., and Vousden, K. H. (2011). Control of glycolysis through regulation of PFK1: old friends and recent additions. *Cold Spring Harb. Symp. Quant. Biol.*, 76, 211-216.

Morgan, D. O. (1997). Cyclin-dependent kinases: engines, clocks, and microprocessors. *Annu. Rev. Cell Dev. Biol.*, 13, 261-291.

Moshinsky, D. J., Bellamacina, C. R., Boisvert, D. C., Huang, P., Hui, T., Jancarik, J., Kim, S.-H., and Rice, A. G. (2003). SU9516: biochemical analysis of cdk inhibition and crystal structure in complex with cdk2. *Biochemical and Biophysical Research Communications*, 310, 1026-1031.

Nierode, G., Kwon, P. S., Dordick, J. S., and Kwon, S.-J. (2016). Cell-Based Assay Design for High-Content Screening of Drug Candidates. *Journal of Microbiology and Biotechnology*, 26, 213-225.

Nomanbhoy, T. K., Sharma, G., Brown, H., Wu, J., Aban, A., Vogeti, S., Alemayehu, S., Sykes, M., Rosenblum, J. S., and Kozarich, J. W. (2016a). Chemoproteomic Evaluation of Target Engagement by the Cyclin-Dependent Kinase 4 and 6 Inhibitor Palbociclib Correlates with Cancer Cell Response. *Biochemistry*, 55, 5434-5441.

Nomanbhoy, T. K., Sharma, G., Brown, H., Wu, J., Aban, A., Vogeti, S., Alemayehu, S., Sykes, M., Rosenblum, J. S., and Kozarich, J. W. (2016b). Chemoproteomic Evaluation of Target Engagement by the Cyclin-Dependent Kinase 4 and 6 Inhibitor Palbociclib Correlates with Cancer Cell Response. *Biochemistry*, 55, 5434-5441.

Roy, D., Sheng, G. Y., Herve, S., Carvalho, E., Mahanty, A., Yuan, S., and Sun, L. (2017). Interplay between cancer cell cycle and metabolism: Challenges, targets and therapeutic opportunities. *Biomed. Pharmacother.*, 89, 288-296.

Salazar-Roa, M., and Malumbres, M. (2017). Fueling the Cell Division Cycle. *Trends in Cell Biology*, 27, 69-81.

Sarathy, A., Wuebbles, R. D., Fontelonga, T. M., Tarchione, A. R., Griner, L. A. M., Heredia, D. J., Nunes, A. M., Duan, S., Brewer, P. D., Van Ry, T., et al. (2017). SU9516 Increases α7β1 Integrin and Ameliorates Disease Progression in the mdx Mouse Model of Duchenne Muscular Dystrophy. *Molecular Therapy*, 25(6), 1395-1407.

Schmitt, D. L., and An, S. (2017). Spatial Organization of Metabolic Enzyme Complexes in Cells. *Biochemistry*, 56, 3184-3196.

Schmitt, D. L., Dranchak, P., Inglese, J., An, S. (2017). Spatial Regulation of Enzyme Compartmentalization of Small Molecules in Live Cells. Poster Presentation, 10$^{th}$ Annual Frontiers at the Chemistry and Biology Interface Symposium, University of Delaware, Newark, Del., May 6, 2017.

Smith, J. A., Poteet-Smith, C. E., Xu, Y., Errington, T. M., Hecht, S. M., and Lannigan, D. A. (2005). Identification of the first specific inhibitor of p90 ribosomal S6 kinase (RSK) reveals an unexpected role for RSK in cancer cell proliferation. *Cancer Research*, 65, 1027-1034.

Southall, N. T., Jadhav, A., Huang, R., Nguyen, T., and Wang, Y. (2009). Enabling the Large-Scale Analysis of Quantitative High-Throughput Screening Data. In Handbook of Drug Screening, (Boca Raton: books.google.co), Seethala, R., Zhang, L., eds., pp. 442-464.

Tandon, P., Gallo, C. A., Khatri, S., Barger, J. F., Yepiskoposyan, H., and Plas, D. R. (2011). Requirement for ribosomal protein S6 kinase 1 to mediate glycolysis and apoptosis resistance induced by Pten deficiency. *Proc. Natl. Acad. Sci. USA.*, 108, 2361-2365.

Uchiyama, H., Sowa, Y., Wakada, M., Yogosawa, M., Nakanishi, R., Horinaka, M., Shimazaki, C., Taniwaki, M., and Sakai, T. (2010). Cyclin-dependent kinase inhibitor SU9516 enhances sensitivity to methotrexate in human T-cell leukemia Jurkat cells. *Cancer Science*, 101, 728-734.

Varoni, E. M., Faro, Lo, A. F., Sharifi-Rad, J., and Iriti, M. (2016). Anticancer Molecular Mechanisms of Resveratrol. *Front. Nutr.*, 3, 84-15.

Wang, B.-Y., Liu, Q.-Y., Cao, J., Chen, J.-W., and Liu, Z.-S. (2016). Selective CDK7 inhibition with BS-181 suppresses cell proliferation and induces cell cycle arrest and apoptosis in gastric cancer. *Drug Des Devel Ther*, 10, 1181-1189.

Webb, B. A., Dosey, A. M., Wittmann, T., Kollman, J. M., and Barber, D. L. (2017). The glycolytic enzyme phosphofructokinase-1 assembles into filaments. *The Journal of Cell Biology*, 258, jcb.201701084-13.

Yalcin, A., Clem, B. F., Imbert-Fernandez, Y., Ozcan, S. C., Peker, S., Neal, J. O. A., Klarer, A. C., Clem, A. L., Telang, S., and Chesney, J. (2014). 6-Phosphofructo-2-kinase (PFKFB3) promotes cell cycle progression and suppresses apoptosis via Cdk1-mediated phosphorylation of p27. *Cell Death and Disease*, 5, e1337-10.

Yu, B., Lane, M. E., and Wadler, S. (2002). SU9516, a cyclin-dependent kinase 2 inhibitor, promotes accumulation of high molecular weight E2F complexes in human colon carcinoma cells. *Biochemical Pharmacology*, 64, 1091-1100.

Zanella, F., Lorens, J. B., and Link, W. (2010). High content screening: seeing is believing. *Trends in Biotechnology*, 28, 237-245.

Zhang, J., Chung, T., and Oldenburg, K. (1999). A Simple Statistical Parameter for Use in Evaluation and Validation of High Throughput Screening Assays. *Journal of Biomolecular Screening*, 4, 67-73.

What is claimed is:

1. An assay method to identify an active testing compound which induces clustering in a host cell, the method comprising:

providing a medium comprising host cells that express phosphofructokinase 1 (PFK1) fused to a fluorescent protein (PFK1-FP);

introducing at least two concentrations of a testing compound into individual aliquots of the medium and incubating same;

imaging the host cells of the incubated medium to identify testing compounds inducing clusters having at least a minimum area and sensitivity; and plotting a quantitative high-throughput screening (qHTS) titration curve of the percent of host cells showing PFK1-FP clustering versus the log compound concentration for the testing compound, wherein the qHTS titration curve of the testing compound includes the titration curve of a positive control compound, wherein the testing compound is considered active when the qHTS titration curve is a full titration curve or a partial titration curve.

2. The assay method of claim 1, wherein the host cells comprise a species selected from the group consisting of Chinese hamster ovary (CHO) cells, HeLa cells, HEK293, baby hamster kidney (BHK) cells, monkey kidney cells (COS), human hepatocellular carcinoma cells, human mammary gland/breast carcinoma cells, Madin-Darby bovine kidney ("MDBK") cells, and NOS cells derived from carcinoma cells.

3. The assay method of claim 1, wherein the host cells comprise a HeLa-T-PFK1G cell line.

4. The assay method of claim 1, wherein the host cells are harvested cells from a specific individual for personalized medicine.

5. The assay method of claim 1, wherein the fluorescent protein is a green fluorescent protein (GFP).

6. The assay method of claim 5, wherein the GFP is a monomeric form of enhanced green fluorescent protein (mEGFP).

7. The assay method of claim 1, wherein a qHTS titration curve class of 1.1, 1.2, 2.1, and 2.2 is indicative of an active testing compound capable of inducing medium- or large-sized PFK1-mEGFP clusters.

8. The assay method of claim 1, wherein the positive control compound comprises a species selected from the group consisting of resveratrol, SU9516, kenpaullone, and olomoucine.

9. The assay of claim 1, wherein the medium is plated in wells of microtiter plates.

10. The assay method of claim 1, wherein clustering is associated with changes in cell cycle progression within the host cell.

11. The assay method of claim 1, wherein the active testing compound may be used to treat cancer.

* * * * *